(12) United States Patent
Abreo et al.

(10) Patent No.: US 7,763,618 B2
(45) Date of Patent: *Jul. 27, 2010

(54) PYRIDYL DERIVATIVES AND THEIR USE AS THERAPEUTIC AGENTS

(75) Inventors: Melwyn Abreo, Jamul, CA (US); Daniel F. Harvey, San Diego, CA (US); Mikhail A. Kondratenko, San Diego, CA (US); Wenbao Li, San Diego, CA (US); Rajender Kamboj, Burnaby (CA); Vishnumurthy Kodumuru, Burnaby (CA); Michael D. Winther, Vancouver (CA); Heinz W. Gschwend, Santa Rosa, CA (US); Nagasree Chakka, Burnaby, CA (US); Shifeng Liu, Port Coquitlam (CA); Serguei Sviridov, Burnaby, CA (US); Shaoyi Sun, Vancouver (CA)

(73) Assignee: Xenon Pharmaceuticals Inc., Burnaby, British Columbia (CA)

( * ) Notice: Subject to any disclaimer, the term of this patent is extended or adjusted under 35 U.S.C. 154(b) by 625 days.

This patent is subject to a terminal disclaimer.

(21) Appl. No.: 10/566,857

(22) PCT Filed: Jul. 29, 2004

(86) PCT No.: PCT/US2004/024542

§ 371 (c)(1),
(2), (4) Date: Jan. 30, 2006

(87) PCT Pub. No.: WO2005/011654

PCT Pub. Date: Feb. 10, 2005

(65) Prior Publication Data

US 2006/0293308 A1 Dec. 28, 2006

Related U.S. Application Data

(60) Provisional application No. 60/491,140, filed on Jul. 29, 2003, provisional application No. 60/491,080, filed on Jul. 30, 2003, provisional application No. 60/491,116, filed on Jul. 30, 2003, provisional application No. 60/491,322, filed on Jul. 30, 2003, provisional application No. 60/491,141, filed on Jul. 30, 2003.

(51) Int. Cl.
*A61K 31/497* (2006.01)
*C07D 241/04* (2006.01)
*C07D 295/00* (2006.01)
(52) U.S. Cl. .................. 514/252.12; 544/358
(58) Field of Classification Search ............ None
See application file for complete search history.

(56) References Cited

U.S. PATENT DOCUMENTS 6,677,452 B1 * 1/2004 Chen et al. ............. 544/365

| 6,777,414 | B1 | 8/2004 | Ohkura et al. |
| 2005/0038035 | A1 | 2/2005 | Takasugi et al. |
| 2005/0119251 | A1 * | 6/2005 | Fu et al. .................. 514/218 |
| 2006/0199802 | A1 * | 9/2006 | Abreo et al. ............ 514/218 |

FOREIGN PATENT DOCUMENTS

| CA | 2361525 A1 | 8/2000 |
| CA | 2369103 A1 | 10/2000 |
| CA | 2448298 A1 | 12/2000 |
| CA | 2468716 A1 | 6/2003 |
| CA | 2512646 A1 | 8/2004 |
| EP | 1 180 514 | 2/2002 |
| EP | 1 396 487 | 3/2004 |
| WO | WO-00/44755 | 8/2000 |
| WO | WO-01/62954 | 8/2001 |
| WO | WO-02/102778 | 12/2002 |
| WO | WO-03/045921 | 6/2003 |
| WO | WO-03/075929 | 9/2003 |
| WO | WO-2004/065378 | 8/2004 |
| WO | 2005011654 A2 | 2/2005 |

OTHER PUBLICATIONS

Stella, V. Expert Opinion in Therapeutic Patents, 2004, 14(3), 277-280.*
U.S. Appl. No. 11/815,739, filed Aug. 2007, Kamboj et al.*
Dobrzyn et al. Expert Opinion in Therapeutic Patents, 2008, 18(4), 457-60.*
Boss et al. Expert Opinion in Therapeutic Targets, 2006, 10(1), 119-134.*
Dobrzyn et al. Obesity reviews, 2005, 6, 169-174.*
Ntambi. Journal of Lipid Research, 1999, 40, 1549-58.*
"Metabolic diseases", http://www.nlm.nih.gov/cgi/mesh/2008/MB_cgi, accessed Feb. 20, 2008.*

(Continued)

*Primary Examiner*—James O Wilson
*Assistant Examiner*—Noble Jarrell
(74) *Attorney, Agent, or Firm*—Osha • Liang LLP

(57) ABSTRACT

Methods of treating an SCD-mediated disease or condition in a mammal, preferably a human, are disclosed, wherein the methods comprise administering to a mammal in need thereof a compound of formula (I): wherein W, V, x, y, $R^1$, $R^2$, $R^3$, $R^4$, $R^5$, $R^6$, $R^7$, $R^{7a}$, $R^8$, $R^{8a}$, $R^9$, $R^{9a}$, $R^{10}$ and $R^{10a}$ are defined herein. Pharmaceutical compositions comprising the compounds of formula (I) are also disclosed.

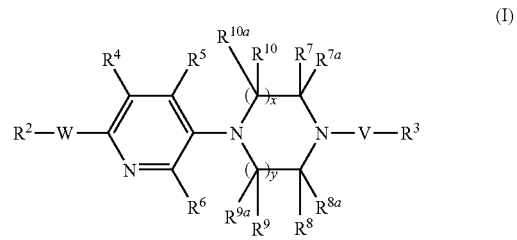

(I)

43 Claims, No Drawings

OTHER PUBLICATIONS

EPO Communication dated Mar. 10, 2008, issued in related European patent application No. EP-04/779556.2-2123 (5 pages) (Please Note: On p. 3, under "Claims, Nos., 2) Cited documents:", that all of these references were previously submitted to the USPTO in the IDS filed with the original Application on Jan. 30, 2006).

International Search Report for PCT/US2004/024542, published on Feb. 10, 2005 (4 pages).

Substantive Examination Adverse Report and Search Report issued Oct. 31, 2008, by the Malaysian Patent Office in related-Malaysian Patent Application No. PI-20060383 (2 pages).

\* cited by examiner

PYRIDYL DERIVATIVES AND THEIR USE AS THERAPEUTIC AGENTS

FIELD OF THE INVENTION

The present invention relates generally to the field of inhibitors of stearoyl-CoA desaturase, such as pyridine derivatives, and uses for such compounds in treating and/or preventing various human diseases, including those mediated by stearoyl-CoA desaturase (SCD) enzymes, preferably SCD1, especially diseases related to elevated lipid levels, cardiovascular disease, diabetes, obesity, metabolic syndrome and the like.

BACKGROUND OF THE INVENTION

Acyl desaturase enzymes catalyze the formation of double bonds in fatty acids derived from either dietary sources or de novo synthesis in the liver. Mammals synthesize at least three fatty acid desaturases of differing chain length specificity that catalyze the addition of double bonds at the delta-9, delta-6, and delta-5 positions. Stearoyl-CoA desaturases (SCDs) introduce a double bond in the C9-C10 position of saturated fatty acids. The preferred substrates are palmitoyl-CoA (16:0) and stearoyl-CoA (18:0), which are converted to palmitoleoyl-CoA (16:1) and oleoyl-CoA (18:1), respectively. The resulting mono-unsaturated fatty acids are substrates for incorporation into phospholipids, triglycerides, and cholesteryl esters.

A number of mammalian SCD genes have been cloned. For example, two genes have been cloned from rat (SCD1, SCD2) and four SCD genes have been isolated from mouse (SCD1, 2, 3, and 4). While the basic biochemical role of SCD has been known in rats and mice since the 1970's (Jeffcoat, R. et al., *Elsevier Science* (1984), Vol. 4, pp. 85-112; de Antueno, R J, *Lipids* (1993), Vol. 28, No. 4, pp. 285-290), it has only recently been directly implicated in human disease processes.

A single SCD gene, SCD1, has been characterized in humans. SCD1 is described in Brownlie et al, PCT published patent application, WO 01/62954, the disclosure of which is hereby incorporated by reference in its entirety. A second human SCD isoform has recently been identified, and because it bears little sequence homology to alternate mouse or rat isoforms it has been named human SCD5 or hSCD5 (PCT published patent application, WO 02/26944, incorporated herein by reference in its entirety).

To date, no small-molecule, drug-like compounds are known that specifically inhibit or modulate SCD activity. Certain long-chain hydrocarbons have been used historically to study SCD activity. Known examples include thia-fatty acids, cyclopropenoid fatty acids, and certain conjugated linoleic acid isomers. Specifically, cis-12, trans-10 conjugated linoleic acid is believed to inhibit SCD enzyme activity and reduce the abundance of SCD1 mRNA while cis-9, trans-11 conjugated linoleic acid does not. Cyclopropenoid fatty acids, such as those found in sterculia and cotton seeds, are also known to inhibit SCD activity. For example, sterculic acid (8-(2-octylcyclopropenyl)octanoic acid) and malvalic acid (7-(2-octylcyclopropenyl)heptanoic acid) are C18 and C16 derivatives of sterculoyl and malvaloyl fatty acids, respectively, having cyclopropene rings at their C9-C10 position. These agents are believed to inhibit SCD enzymatic activity by direct interaction with the enzyme, thus inhibiting delta-9 desaturation. Other agents that may inhibit SCD activity include thia-fatty acids, such as 9-thiastearic acid (also called 8-nonylthiooctanoic acid) and other fatty acids with a sulfoxy moiety.

These known modulators of delta-9 desaturase activity are not useful for treating the diseases and disorders linked to SCD1 biological activity. None of the known SCD inhibitor compounds are selective for SCD or delta-9 desaturases, as they also inhibit other desaturases and enzymes. The thiafatty acids, conjugated linoleic acids and cyclopropene fatty acids (malvalic acid and sterculic acid) are neither useful at reasonable physiological doses, nor are they specific inhibitors of SCD1 biological activity, rather they demonstrate cross inhibition of other desaturases, in particular the delta-5 and delta-6 desaturases by the cyclopropene fatty acids.

The absence of small molecule inhibitors of SCD enzyme activity is a major scientific and medical disappointment because evidence is now compelling that SCD activity is directly implicated in common human disease processes: See e.g., Attie, A. D. et al., "Relationship between stearoyl-CoA desaturase activity and plasma triglycerides in human and mouse hypertriglyceridemia", *J. Lipid Res.* (2002), Vol. 43, No. 11, pp. 1899-907; Cohen, P. et al., "Role for stearoyl-CoA desaturase-1 in leptin-mediated weight loss", *Science* (2002), Vol. 297, No. 5579, pp. 240-3, Ntambi, J. M. et al., "Loss of stearoyl-CoA desaturase-1 function protects mice against adiposity", *Proc. Natl. Acad. Sci. USA.* (2002), Vol. 99, No. 7, pp. 11482-6.

The present invention solves this problem by presenting new classes of compounds that are useful in modulating SCD activity and regulating lipid levels, especially plasma lipid levels, and which are useful in the treatment of SCD-mediated diseases such as diseases related to dyslipidemia and disorders of lipid metabolism, especially diseases related to elevated lipid levels, cardiovascular disease, diabetes, obesity, metabolic syndrome and the like.

Related Literature

PCT Published Patent Application WO 01/96327 discloses novel benzamide derivative compounds. PCT Published Patent Applications, WO 03/075929, WO 03/076400 and WO 03/076401, disclose compounds having histone deacetylase inhibiting enzymatic activity.

BRIEF SUMMARY OF THE INVENTION

The present invention provides pyridine derivatives that modulate the activity of stearoyl-CoA desaturase. Methods of using such derivatives to modulate the activity of stearoyl-CoA desaturase and pharmaceutical compositions comprising such derivatives are also encompassed.

Accordingly, in one aspect, the invention provides methods of inhibiting human stearoyl-CoA desaturase (hSCD) activity comprising contacting a source of hSCD with a compound of formula (I):

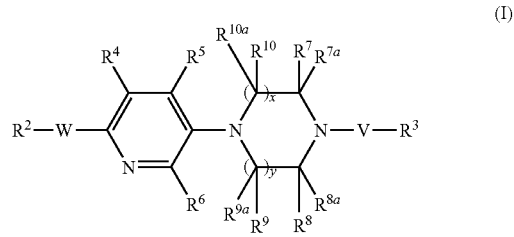

wherein:

x and y are each independently 1, 2 or 3;

W is —O—, —N($R^1$)—, —C(O)—, —S(O)$_t$—; (where t is 0, 1 or 2), —N($R^1$)S(O)$_2$—, —S(O)$_2$N($R^1$)—, —OS(O)$_2$N ($R^1$)—, —C(O)N($R^1$)—, —OC(O)N($R^1$)—, —C(S)N ($R^1$)—, —OC(S)N($R^1$)—, —N($R^1$)C(O)— or —N($R^1$)C(O)N($R^1$)—;

V is —C(O)—, —C(S)—, —C(O)N($R^1$)—, —C(O)O—, —S(O)$_2$—, —S(O)$_2$N($R^1$)— or —C($R^{11}$)H—;

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$, $R^5$ and $R^6$ are each independently selected from hydrogen, fluoro, chloro, methyl, methoxy, trifluoromethyl, cyano, nitro or —N($R^{13}$)$_2$;

$R^7$, $R^{7a}$, $R^8$, $R^{8a}$, $R^9$, $R^{9a}$, $R^{10}$ and $R^{10a}$ are each independently selected from hydrogen or $C_1$-$C_3$alkyl;

or $R^7$ and $R^{7a}$ together, or $R^8$ and $R^{8a}$ together, or $R^9$ and $R^{9a}$ together, or $R^{10}$ and $R^{10a}$ together are an oxo group, provided that when V is —C(O)—, $R^7$ and $R^{7a}$ together or $R^8$ and $R^{8a}$ together do not form an oxo group, while the remaining $R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl;

or one of $R^{10}$, $R^{10a}$, $R^7$, and $R^{7a}$ together with one of $R^8$, $R^{8a}$, $R^9$ and $R^{9a}$ form an alkylene bridge, while the remaining $R^{10}$, $R^{10a}$, $R^7$, $R^{7a}$, $R^8$, $R^{8a}$, $R^9$, and $R^{9a}$ are each independently selected from hydrogen or $C_1$-$C_3$alkyl;

$R^{11}$ is hydrogen or $C_1$-$C_3$alkyl; and each $R^{13}$ is independently selected from hydrogen or $C_1$-$C_6$alkyl;

a stereoisomer, enantiomer or tautomer thereof, a pharmaceutically acceptable salt thereof, a pharmaceutical composition thereof or a prodrug thereof.

In another aspect, the invention provides methods of treating a disease or condition mediated by stearoyl-CoA desaturase (SCD) in a mammal, wherein the method comprises administering to the mammal in need thereof a therapeutically effective amount of a compound of formula (I) as set forth above.

In another aspect, the invention provides compounds of formula (I) having the following formula (IIa):

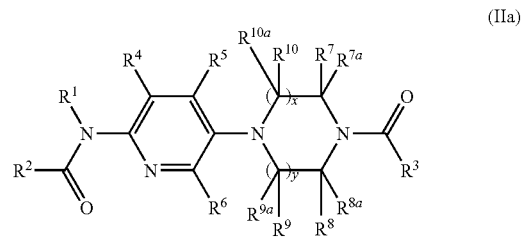

(IIa)

wherein:

x and y are each independently 1, 2 or 3;

$R^1$ is selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_7$-$C_{12}$alkyl, $C_3$-$C_{12}$alkenyl, $C_7$-$C_{12}$hydroxyalkyl, $C_1$-$C_{12}$alkoxy, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_1$-$C_{12}$heteroaryl, $C_3$-$C_{12}$heterocyclylalkyl and $C_3$-$C_{12}$heteroarylalkyl, provided that $R^2$ is not pyrazinyl, pyridinonyl, pyrrolidinone or imidazolyl;

or $R^2$ is a multi-ring structure having 2 to 4 rings wherein the rings are independently selected from the group consisting of cycloalkyl, heterocyclyl, aryl and heteroaryl, where some or all of the rings may be fused to each other;

$R^3$ is selected from the group consisting of $C_3$-$C_{12}$alkyl, $C_3$-$C_{12}$alkenyl, $C_3$-$C_{12}$hydroxyalkyl, $C_3$-$C_{12}$hydroxyalkenyl, $C_3$-$C_{12}$alkoxy, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

$R^4$, $R^5$ and $R^6$ are each independently selected from hydrogen, fluoro, chloro, methyl, methoxy, trifluoromethyl, cyano, nitro or —N($R^{13}$)$_2$;

$R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl;

or $R^9$ and $R^{9a}$ together, or $R^{10}$ and $R^{10a}$ together form an oxo group, while the remaining $R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl;

or one of $R^7$, $R^{7a}$, $R^{10}$ and $R^{10a}$, together with one of $R^8$, $R^{8a}$, $R^9$ and $R^{9a}$, form an alkylene bridge, while the remaining $R^{10}$, $R^{10a}$, $R^7$, $R^{7a}$, $R^8$, $R^{8a}$, $R^9$, and $R^{9a}$ are each independently selected from hydrogen or $C_1$-$C_3$alkyl; and each $R^{13}$ is independently selected from hydrogen or $C_1$-$C_6$alkyl;

a stereoisomer, enantiomer or tautomer thereof, a pharmaceutically acceptable salt thereof, a pharmaceutical composition thereof or a prodrug thereof.

In another aspect, the invention provides compounds of formula (I) having the following formula (IIb):

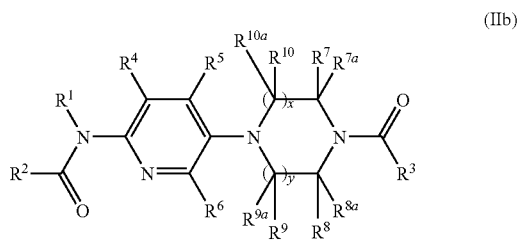

(IIb)

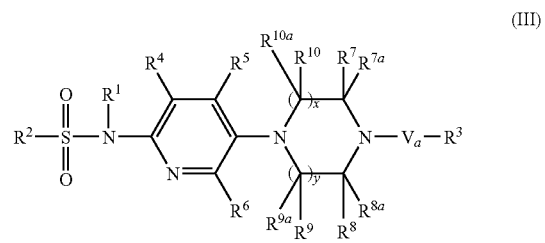

(III)

wherein:

x and y are each independently 1, 2 or 3;

$R^1$ is selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl;

or $R^2$ is phenyl optionally substituted with one or more substituents selected from halo and $C_1$-$C_6$trihaloalkyl;

or $R^2$ is a multi-ring structure having 2 to 4 rings wherein the rings are independently selected from the group consisting of cycloalkyl, heterocyclyl, aryl and heteroaryl, where some or all of the rings may be fused to each other;

$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl, provided that $R^3$ is not phenyl substituted with optionally substituted thienyl;

$R^4$, $R^5$ and $R^6$ are each independently selected from hydrogen, fluoro, chloro, methyl, methoxy, trifluoromethyl, cyano, nitro or —N($R^{13}$)$_2$;

$R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl;

or $R^9$ and $R^{9a}$ together, or $R^{10}$ and $R^{10a}$ together form an oxo group, while the remaining $R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl;

or one of $R^7$, $R^{7a}$, $R^{10}$ and $R^{10a}$, together with one of $R^8$, $R^{8a}$, $R^9$ and $R^{9a}$, form an alkylene bridge, while the remaining $R^{10}$, $R^{10a}$, $R^7$, $R^{7a}$, $R^8$, $R^{8a}$, $R^9$, and $R^{9a}$ are each independently selected from hydrogen or $C_1$-$C_3$alkyl; and each $R^{12}$ is independently selected from hydrogen, $C_1$-$C_6$alkyl, $C_3$-$C_6$cycloalkyl, aryl or aralkyl; and each $R^{13}$ is independently selected from hydrogen or $C_1$-$C_6$alkyl;

a stereoisomer, enantiomer or tautomer thereof, a pharmaceutically acceptable salt thereof, a pharmaceutical composition thereof or a prodrug thereof.

In another aspect, the invention provides compounds of formula (I) having the following formula (III):

wherein:

x and y are each independently 1, 2 or 3;

$V_a$ is —C(O)—, —C(S)—, —C(O)N($R^1$)—, —C(O)O—, —S(O)$_2$— or —S(O)$_2$N($R^1$)—;

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl, where some or all of the rings may be fused to each other;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$, $R^5$ and $R^6$ are each independently selected from hydrogen, fluoro, chloro, methyl, methoxy, trifluoromethyl, cyano, nitro or —N($R^{13}$)$_2$;

$R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl;

or $R^7$ and $R^{7a}$ together, or $R^8$ and $R^{8a}$ together, or $R^9$ and $R^{9a}$ together, or $R^{10}$ and $R^{10a}$ together are an oxo group, provided that when $V_a$ is —C(O)—, $R^7$ and $R^{7a}$ together or $R^8$ and $R^{8a}$ together do not form an oxo group, while the remaining $R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl;

or one of $R^{10}$, $R^{10a}$, $R^7$, and $R^{7a}$ together with one of $R^8$, $R^{8a}$, $R^9$ and $R^{9a}$ form an alkylene bridge, while the remaining $R^{10}$, $R^{10a}$, $R^7$, $R^{7a}$, $R^8$, $R^{8a}$, $R^9$, and $R^{9a}$ are each independently selected from hydrogen or $C_1$-$C_3$alkyl; and each $R^{13}$ is independently selected from hydrogen or $C_1$-$C_6$alkyl;

a stereoisomer, enantiomer or tautomer thereof, a pharmaceutically acceptable salt thereof, a pharmaceutical composition thereof or a prodrug thereof.

In another aspect, the invention provides compounds of formula (I) having the following formula (IV):

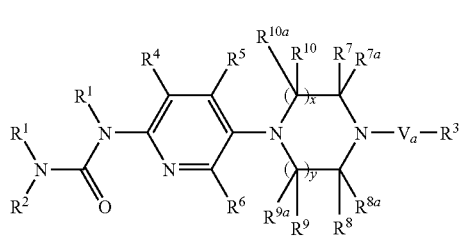

(IV)

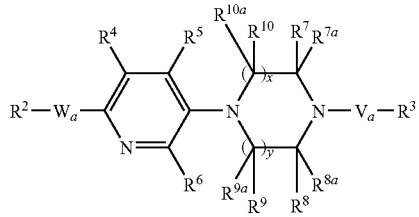

(V)

wherein:

x and y are each independently 1, 2 or 3;

$V_a$ is —C(O)—, —C(S)—, —C(O)N($R^1$)—, —C(O)O—, —S(O)$_2$— or —S(O)$_2$N($R^1$)—;

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl, where some or all of the rings may be fused to each other;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$, $R^5$ and $R^6$ are each independently selected from hydrogen, fluoro, chloro, methyl, methoxy, trifluoromethyl, cyano, nitro or —N($R^{13}$)$_2$;

$R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl;

or $R^7$ and $R^{7a}$ together, or $R^8$ and $R^{8a}$ together, or $R^9$ and $R^{9a}$ together, or $R^{10}$ and $R^{10a}$ together are an oxo group, provided that when $V_a$ is —C(O)—, $R^7$ and $R^{7a}$ together or $R^8$ and $R^{8a}$ together do not form an oxo group, while the remaining $R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl;

or one of $R^{10}$, $R^{10a}$, $R^7$, and $R^{7a}$ together with one of $R^8$, $R^{8a}$, $R^9$ and $R^{9a}$ form an alkylene bridge, while the remaining $R^{10}$, $R^{10a}$, $R^7$, $R^{7a}$, $R^8$, $R^{8a}$, $R^9$, and $R^{9a}$ are each independently selected from hydrogen or $C_1$-$C_3$alkyl; and each $R^{13}$ is independently selected from hydrogen or $C_1$-$C_6$alkyl;

a stereoisomer, enantiomer or tautomer thereof, a pharmaceutically acceptable salt thereof, a pharmaceutical composition thereof or a prodrug thereof.

In another aspect, the invention provides compounds of formula (I) having the following formula (V):

wherein:

x and y are each independently 1, 2 or 3;

$W_a$ is —O—, —N($R^1$)— or —S(O)$_t$— (where t is 0, 1 or 2);

$V_a$ is —C(O)—, —C(S)—, —C(O)N($R^1$)—, —C(O)O—, —S(O)$_2$— or —S(O)$_2$N($R^1$)—;

x and y are each independently 1, 2 or 3;

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl, where some or all of the rings may be fused to each other;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$, $R^5$ and $R^6$ are each independently selected from hydrogen, fluoro, chloro, methyl, methoxy, trifluoromethyl, cyano, nitro or —N($R^{13}$)$_2$;

$R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl;

or $R^7$ and $R^{7a}$ together, or $R^8$ and $R^{8a}$ together, or $R^9$ and $R^{9a}$ together, or $R^{10}$ and $R^{10a}$ together are an oxo group, provided that when $V_a$ is —C(O)—, $R^7$ and $R^{7a}$ together or $R^8$ and $R^{8a}$ together do not form an oxo group, while the remaining $R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl;

or one of $R^{10}$, $R^{10a}$, $R^7$, and $R^{7a}$ together with one of $R^8$, $R^{8a}$, $R^9$ and $R^{9a}$ form an alkylene bridge, while the remaining $R^{10}$, $R^{10a}$, $R^7$, $R^{7a}$, $R^8$, $R^{8a}$, $R^9$, and $R^{9a}$ are each independently selected from hydrogen or $C_1$-$C_3$alkyl; and each $R^{13}$ is independently selected from hydrogen or $C_1$-$C_6$alkyl;

a stereoisomer, enantiomer or tautomer thereof, a pharmaceutically acceptable salt thereof, a pharmaceutical composition thereof or a prodrug thereof.

In another aspect, the invention provides compounds of formula (I) having the following formula (VIa):

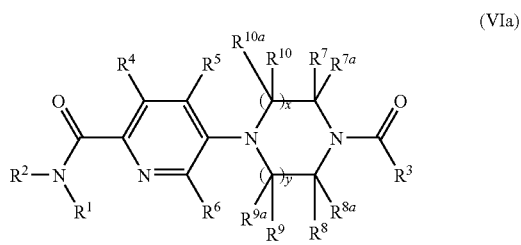

(VIa)

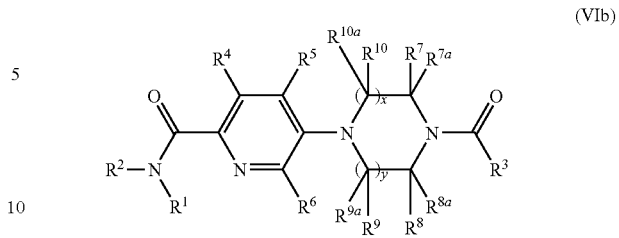

(VIb)

wherein:

x and y are each independently 1, 2 or 3;

$R^1$ is selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_7$-$C_{12}$alkyl, $C_3$-$C_{12}$alkenyl, $C_7$-$C_{12}$hydroxyalkyl, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_3$-$C_{12}$heterocyclylalkyl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl, where some or all of the rings may be fused to each other;

$R^3$ is selected from the group consisting of $C_3$-$C_{12}$alkyl, $C_3$-$C_{12}$alkenyl, $C_3$-$C_{12}$hydroxyalkyl, $C_3$-$C_{12}$hydroxyalkenyl, $C_3$-$C_{12}$alkoxy, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_5$-$C_{12}$ heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$, $R^5$ and $R^6$ are each independently selected from hydrogen, fluoro, chloro, methyl, methoxy, trifluoromethyl, cyano, nitro or —N($R^{13}$)$_2$;

$R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl;

or $R^7$ and $R^{7a}$ together, or $R^8$ and $R^{8a}$ together, or $R^9$ and $R^{9a}$ together, or $R^{10}$ and $R^{10a}$ together are an oxo group, provided that when $V_a$ is —C(O)—, $R^7$ and $R^{7a}$ together or $R^8$ and $R^{8a}$ together do not form an oxo group, while the remaining $R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl;

or one of $R^{10}$, $R^{10a}$, $R^7$, and $R^{7a}$ together with one of $R^8$, $R^{8a}$, $R^9$, and $R^{9a}$ form an alkylene bridge, while the remaining $R^{10}$, $R^{10a}$, $R^7$, $R^{7a}$, $R^8$, $R^{8a}$, $R^9$, and $R^{9a}$ are each independently selected from hydrogen or $C_1$-$C_3$alkyl; and each $R^{13}$ is independently selected from hydrogen or $C_1$-$C_6$alkyl;

including a stereoisomer, enantiomer or tautomer thereof, a pharmaceutically acceptable salt thereof, a pharmaceutical composition thereof or a prodrug thereof.

In another aspect, the invention provides compounds of formula (I) having the following formula (VIb):

wherein:

x and y are each independently 1, 2 or 3;

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl, where some or all of the rings may be fused to each other;

$R^3$ is naphthyl or phenyl, each optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)N($R^{12}$)$_2$, cycloalkyl, heterocyclyl, heteroaryl and heteroarylcycloalkyl, provided that $R^3$ is not phenyl substituted with optionally substituted thienyl, and provided that when $R^3$ is naphthyl, $R^2$ can not be $C_1$-$C_6$alkyl, $C_2$-$C_6$hydroxyalkyl or phenyl substituted by amino;

$R^4$, $R^5$ and $R^6$ are each independently selected from hydrogen, fluoro, chloro, methyl, methoxy, trifluoromethyl, cyano, nitro or —N($R^{13}$)$_2$;

$R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl;

or $R^7$ and $R^{7a}$ together, or $R^8$ and $R^{8a}$ together, or $R^9$ and $R^{9a}$ together, or $R^{10}$ and $R^{10a}$ together are an oxo group, provided that when $V_a$ is —C(O)—, $R^7$ and $R^{7a}$ together or $R^8$ and $R^{8a}$ together do not form an oxo group, while the remaining $R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl;

or one of $R^{10}$, $R^{10a}$, $R^7$, and $R^{7a}$ together with one of $R^8$, $R^{8a}$, $R^9$ and $R^{9a}$ form an alkylene bridge, while the remaining $R^{10}$, $R^{10a}$, $R^7$, $R^{7a}$, $R^8$, $R^{8a}$, $R^9$, and $R^{9a}$ are each independently selected from hydrogen or $C_1$-$C_3$alkyl;

each $R^{12}$ is independently selected from hydrogen, $C_1$-$C_6$alkyl, $C_3$-$C_6$cycloalkyl, aryl or aralkyl; and each $R^{13}$ is independently selected from hydrogen or $C_1$-$C_6$alkyl;

a stereoisomer, enantiomer or tautomer thereof, a pharmaceutically acceptable salt thereof, a pharmaceutical composition thereof or a prodrug thereof.

In another aspect, the invention provides methods of treating an SCD-mediated disease or condition in a mammal, preferably a human, wherein the methods comprise administering to the mammal in need thereof a therapeutically effective amount of a compound of the invention as set forth above In another aspect, the invention provides compounds or pharmaceutical compositions useful in treating, preventing and/or diagnosing a disease or condition relating to SCD biological activity such as the diseases encompassed by cardiovascular disorders and/or metabolic syndrome (including dyslipidemia, insulin resistance and obesity).

In another aspect, the invention provides methods of preventing or treating a disease or condition related to elevated lipid levels, such as plasma lipid levels, especially elevated triglyceride or cholesterol levels, in a patient afflicted with such elevated levels, comprising administering to said patient a therapeutically or prophylactically effective amount of a composition as disclosed herein. The present invention also relates to novel compounds having therapeutic ability to reduce lipid levels in an animal, especially triglyceride and cholesterol levels.

In another aspect, the invention provides pharmaceutical compositions comprising the compounds of the invention as set forth above, and pharmaceutically acceptable excipients. In one embodiment, the present invention relates to a pharmaceutical composition comprising a compound of the invention in a pharmaceutically acceptable carrier and in an amount effective to modulate triglyceride level, or to treat diseases related to dyslipidemia and disorders of lipid metabolism, when administered to an animal, preferably a mammal, most preferably a human patient. In an embodiment of such composition, the patient has an elevated lipid level, such as elevated plasma triglycerides or cholesterol, before administration of said compound and said compound is present in an amount effective to reduce said lipid level.

In another aspect, the invention provides methods for treating a patient for, or protecting a patient from developing, a disease or condition mediated by stearoyl-CoA desaturase (SCD), which methods comprise administering to a patient afflicted with such disease or condition, or at risk of developing such disease or condition, a therapeutically effective amount of a compound that inhibits activity of SCD in a patient when administered thereto.

In another aspect, the invention provides methods for treating a range of diseases involving lipid metabolism utilizing compounds identified by the methods disclosed herein. In accordance therewith, there is disclosed herein a range of compounds having said activity, based on a screening assay for identifying, from a library of test compounds, a therapeutic agent which modulates the biological activity of said SCD and is useful in treating a human disorder or condition relating to serum levels of lipids, such as triglycerides, VLDL, HDL, LDL, and/or total cholesterol.

DETAILED DESCRIPTION OF THE INVENTION

Definitions

As used in the specification and appended claims, unless specified to the contrary, the following terms have the meaning indicated:

Certain chemical groups named herein are preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

Accordingly, as used in the specification and appended claims, unless specified to the contrary, the following terms have the meaning indicated:

"Methoxy" refers to the —OCH$_3$ radical.
"Cyano" refers to the —CN radical.
"Nitro" refers to the —NO$_2$ radical.
"Trifluoromethyl" refers to the —CF$_3$ radical.
"Oxo" refers to the =O substituent.
"Thioxo" refers to the =S substituent.

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, an alkyl group may be optionally substituted by one of the following groups: alkyl, alkenyl, halo, haloalkenyl, cyano, nitro, aryl, cycloalkyl, heterocyclyl, heteroaryl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$) (where t is 1 to 2), —S(O)$_t$OR$^{16}$ (where t is 1 to 2), —S(O)$_t$R$^{16}$ (where t is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and each R$^{16}$ is alkyl, haloalkyl, cycloalkyl, cycloalkylalkyl, aryl, aralkyl, heterocyclyl, heterocylylalkyl, heteroaryl or heteroarylalkyl, and where each of the above substituents is unsubstituted unless otherwise indicated.

"$C_1$-$C_3$alkyl" refers to an alkyl radical as defined above containing one to three carbon atoms. The $C_1$-$C_3$alkyl radical may be optionally substituted as defined for an alkyl group.

"$C_1$-$C_6$alkyl" refers to an alkyl radical as defined above containing one to six carbon atoms. The $C_1$-$C_6$alkyl radical may be optionally substituted as defined for an alkyl group.

"$C_1$-$C_{12}$alkyl" refers to an alkyl radical as defined above containing one to twelve carbon atoms. The $C_1$-$C_{12}$alkyl radical may be optionally substituted as defined for an alkyl group.

"$C_2$-$C_6$alkyl" refers to an alkyl radical as defined above containing two to six carbon atoms. The $C_2$-$C_6$alkyl radical may be optionally substituted as defined for an alkyl group.

"$C_3$-$C_6$alkyl" refers to an alkyl radical as defined above containing three to six carbon atoms. The $C_3$-$C_6$alkyl radical may be optionally substituted as defined for an alkyl group.

"$C_3$-$C_{12}$alkyl" refers to an alkyl radical as defined above containing three to twelve carbon atoms. The $C_3$-$C_{12}$alkyl radical may be optionally substituted as defined for an alkyl group.

"$C_6$-$C_{12}$alkyl" refers to an alkyl radical as defined above containing six to twelve carbon atoms. The $C_6$-$C_{12}$alkyl radical may be optionally substituted as defined for an alkyl group.

"$C_7$-$C_{12}$alkyl" refers to an alkyl radical as defined above containing seven to twelve carbon atoms. The $C_7$-$C_{12}$alkyl radical may be optionally substituted as defined for an alkyl group.

"Alkenyl" refers to a straight or branched hydrocarbon chain radical group consisting solely of carbon and hydrogen atoms, containing at least one double bond, having from two to twelve carbon atoms, preferably one to eight carbon atoms and which is attached to the rest of the molecule by a single bond, e.g., ethenyl, prop-1-enyl, but-1-enyl, pent-1-enyl, penta-1,4dienyl, and the like. Unless stated otherwise specifically in the specification, an alkenyl group may be optionally substituted by one of the following groups: alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$) (where t is 1 to 2), —S(O)$_t$OR$^{16}$ (where t is 1 to 2), —S(O)$_t$R$^{16}$ (where t is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocylylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"C$_3$-C$_{12}$alkenyl" refers to an alkenyl radical as defined above containing three to 12 carbon atoms. The C$_3$-C$_{12}$alkenyl radical may be optionally substituted as defined for an alkenyl group.

"C$_2$-C$_{12}$alkenyl" refers to an alkenyl radical as defined above containing two to 12 carbon atoms. The C$_2$-C$_{12}$alkenyl radical may be optionally substituted as defined above for an alkenyl group.

"Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons, e.g., methylene, ethylene, propylene, n-butylene, and the like. The alkylene chain may be attached to the rest of the molecule and to the radical group through one carbon within the chain or through any two carbons within the chain.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

"Alkylene bridge" refers to a straight or branched divalent hydrocarbon bridge, linking two different carbons of the same ring structure, consisting solely of carbon and hydrogen, containing no unsaturation and having from one to twelve carbon atoms, preferably having from one to eight carbons, e.g., methylene, ethylene, propylene, n-butylene, and the like. The alkylene bridge may link any two carbons within the ring structure.

"Alkoxy" refers to a radical of the formula —OR$_a$ where R$_a$ is an alkyl radical as defined above. The alkyl part of the alkoxy radical may be optionally substituted as defined above for an alkyl radical.

"C$_1$-C$_6$alkoxy" refers to an alkoxy radical as defined above containing one to six carbon atoms. The alkyl part of the C$_1$-C$_6$alkoxy radical may be optionally substituted as defined above for an alkyl group.

"C$_1$-C$_{12}$alkoxy" refers to an alkoxy radical as defined above containing one to twelve carbon atoms. The alkyl part of the C$_1$-C$_{12}$alkoxy radical may be optionally substituted as defined above for an alkyl group.

"C$_3$-C$_{12}$alkoxy" refers to an alkoxy radical as defined above containing three to twelve carbon atoms. The alkyl part of the C$_3$-C$_{12}$alkoxy radical may be optionally substituted as defined above for an alkyl group.

"Alkoxyalkyl" refers to a radical of the formula —R$_a$—O—R$_a$ where each R$_a$ is independently an alkyl radical as defined above. The oxygen atom may be bonded to any carbon in either alkyl radical. Each alkyl part of the alkoxyalkyl radical may be optionally substituted as defined above for an alkyl group.

"C$_2$-C$_{12}$alkoxyalkyl" refers to an alkoxyalkyl radical as defined above containing two to twelve carbon atoms. Each alkyl part of the C$_2$-C$_{12}$alkoxyalkyl radical may be optionally substituted as defined above for an alkyl group.

"C$_3$alkoxyalkyl" refers to an alkoxyalkyl radical as defined above containing three carbon atoms. Each alkyl part of the C$_3$alkoxyalkyl radical may be optionally substituted as defined above for an alkyl group.

"C$_3$-C$_{12}$alkoxyalkyl" refers to an alkoxyalkyl radical as defined above containing three to twelve carbon atoms. Each alkyl part of the C$_3$-C$_{12}$alkoxyalkyl radical may be optionally substituted as defined above for an alkyl group.

"Alkylsulfonyl" refers to a radical of the formula —S(O)$_2$R$_a$ where R$_a$ is an alkyl group as defined above. The alkyl part of the alkylsulfonyl radical may be optionally substituted as defined above for an alkyl group.

"C$_1$-C$_6$alkylsulfonyl" refers to an alkylsulfonyl radical as defined above having one to six carbon atoms. The C$_1$-C$_6$alkylsulfonyl group may be optionally substituted as defined above for an alkylsulfonyl group.

"Aryl" refers to aromatic monocyclic or multicyclic hydrocarbon ring system consisting only of hydrogen and carbon and containing from 6 to 19 carbon atoms, preferably 6 to 10 carbon atoms, where the ring system may be partially or fully saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)R$^{14}$, —R$^{15}$—C(O)N(R$^{14}$)$_2$, —R$^{15}$—N(R$^{14}$)C(O)OR$^{16}$, —R$^{15}$—N(R$^{14}$)C(O)R$^{16}$, —R$^{15}$—N(R$^{14}$)(S(O)$_t$R$^{16}$) (where t is 1 to 2), —R$^{15}$—S(O)$_t$OR$^{16}$ (where t is 1 to 2), —R$^{15}$—S(O)$_t$R$^{16}$ (where t is 0 to 2), and —R$^{15}$—S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"Aralkyl" refers to a radical of the formula —R$_a$R$_b$ where R$_a$ is an alkyl radical as defined above and R$_b$ is one or more aryl radicals as defined above, e.g., benzyl, diphenylmethyl and the like. The aryl part of the aralkyl radical may be optionally substituted as described above for an aryl group. The alkyl part of the aralkyl radical may be optionally substituted as defined above for an alkyl group.

"C$_7$-C$_{12}$aralkyl" refers to an aralkyl group as defined above containing seven to twelve carbon atoms. The aryl part of the C$_7$-C$_{12}$aralkyl radical may be optionally substituted as described above for an aryl group. The alkyl part of the C$_7$-C$_{12}$aralkyl radical may be optionally substituted as defined above for an alkyl group.

"C$_7$-C$_{19}$aralkyl" refers to an aralkyl group as defined above containing seven to nineteen carbon atoms. The aryl part of the $C_7$-$C_{19}$aralkyl radical may be optionally substituted as described above for an aryl group. The alkyl part of the $C_7$-$C_{19}$aralkyl radical may be optionally substituted as defined above for an alkyl group.

"$C_{13}$-$C_{19}$aralkyl" refers to an aralkyl group as defined above containing thirteen to nineteen carbon atoms. The aryl part of the $C_{13}$-$C_{19}$aralkyl radical may be optionally substituted as described above for an aryl group. The alkyl part of the $C_{13}$-$C_{19}$aralkyl radical may be optionally substituted as defined above for an alkyl group.

"Aralkenyl" refers to a radical of the formula —$R_c R_b$ where $R_c$ is an alkenyl radical as defined above and $R_b$ is one or more aryl radicals as defined above, which may be optionally substituted as described above. The aryl part of the aralkenyl radical may be optionally substituted as described above for an aryl group. The alkenyl part of the aralkenyl radical may be optionally substituted as defined above for an alkenyl group.

"Aryloxy" refers to a radical of the formula —$OR_b$ where $R_b$ is an aryl group as defined above. The aryl part of the aryloxy radical may be optionally substituted as defined above.

"Aryl-$C_1$-$C_6$alkyl" refers to a radical of the formula —$R_h$—$R_i$ where $R_h$ is an unbranched alkyl radical having one to six carbons and $R_i$ is an aryl group attached to the terminal carbon of the alkyl radical.

"Cycloalkyl" refers to a stable non-aromatic monocyclic or bicyclic hydrocarbon radical consisting solely of carbon and hydrogen atoms, having from three to fifteen carbon atoms, preferably having from three to twelve carbon atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, —$R^{15}$—$N(R^4)_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$ (where t is 1 to 2), —$R^{15}$—$S(O)_tOR^{16}$ (where t is 1 to 2), —$R^{15}$—$S(O)_tR^{16}$ (where t is 0 to 2), and —$R^{15}$—$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_6$cycloalkyl" refers to a cycloalkyl radical as defined above having three to six carbon atoms. The $C_3$-$C_6$cycloalkyl radical may be optionally substituted as defined above for a cycloalkyl group.

"$C_3$-$C_{12}$cycloalkyl" refers to a cycloalkyl radical as defined above having three to twelve carbon atoms. The $C_3$-$C_{12}$cycloalkyl radical may be optionally substituted as defined above for a cycloalkyl group.

"Cycloalkylalkyl" refers to a radical of the formula —$R_a R_d$ where $R_a$ is an alkyl radical as defined above and $R_d$ is a cycloalkyl radical as defined above. The cycloalkyl part of the cycloalkyl radical may be optionally substituted as defined above for a cycloalkyl radical. The alkyl part of the cycloalkyl radical may be optionally substituted as defined above for an alkyl radical.

"$C_4$-$C_{12}$cycloalkylalkyl" refers to a cycloalkylalkyl radical as defined above having four to twelve carbon atoms. The $C_4$-$C_{12}$cycloalkylalkyl radical may be optionally substituted as defined above for a cycloalkylalkyl group.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above, e.g., 2-bromoethenyl, 3bromoprop-1-enyl, and the like. The alkenyl part of the haloalkenyl radical may be optionally substituted as defined above for an alkyl group.

"Heterocyclyl" refers to a stable 3 to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14})_2$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$ (where t is 1 to 2), —$R^{15}$—$S(O)_tOR^{16}$ (where t is 1 to 2), —$R^{15}$—$S(O)_tR^{16}$ (where t is 0 to 2), and —$R^{15}$—$S(O)_tN(R^{14})_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_{12}$heterocyclyl" refers to a heterocyclyl radical as defined above having three to twelve carbons. The $C_3$-$C_{12}$heterocyclyl may be optionally substituted as defined above for a heterocyclyl group.

"Heterocyclylalkyl" refers to a radical of the formula —$R_a R_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"$C_3$-$C_{12}$heterocyclylalkyl" refers to a heterocyclylalkyl radical as defined above having three to twelve carbons. The $C_3$-$C_{12}$heterocyclylalkyl radical may be optionally substituted as defined above for a heterocyclylalkyl group.

"Heteroaryl" refers to a 5- to 18-membered aromatic ring radical which consists of carbon atoms and from one to five heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$, —$R^{15}$—N($R^{14}$)$_2$, —$R^{15}$—C(O)$R^{14}$, —$R^{15}$—C(O)$OR^{14}$, —$R^{15}$—C(O)N($R^{14}$)$_2$, —$R^{15}$—N($R^{14}$)C(O)$OR^{16}$, —$R^{15}$—N($R^{14}$)C(O)$R^{16}$, —$R^{15}$—N($R^{14}$)(S(O)$_t$$R^{16}$) (where t is 1 to 2), —$R^{15}$—S(O)$_t$$OR^{16}$ (where t is 1 to 2), —$R^{15}$—S(O)$_t$$R^{16}$ (where t is 0 to 2), and —$R^{15}$—S(O)$_t$N($R^{14}$)$_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_1$-$C_{12}$heteroaryl" refers to a heteroaryl radical as defined above having one to twelve carbon atoms. The $C_1$-$C_{12}$heteroaryl group may be optionally substituted as defined above for a heteroaryl group.

"$C_5$-$C_{12}$heteroaryl" refers to a heteroaryl radical as defined above having five to twelve carbon atoms. The $C_5$-$C_{12}$heteroaryl group may be optionally substituted as defined above for a heteroaryl group.

"Heteroarylalkyl" refers to a radical of the formula —$R_a R_f$ where $R_a$ is an alkyl radical as defined above and $R_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"$C_3$-$C_{12}$heteroarylalkyl" refers to a heteroarylalkyl radical as defined above having three to twelve carbon atoms. The $C_3$-$C_{12}$heteroarylalkyl group may be optionally substituted as defined above for a heteroarylalkyl group.

"Heteroarylcycloalkyl" refers to a radical of the formula —$R_d R_f$ where $R_d$ is a cycloalkyl radical as defined above and $R_f$ is a heteroaryl radical as defined above. The cycloalkyl part of the heteroarylcycloalkyl radical may be optionally substituted as defined above for a cycloalkyl group. The heteroaryl part of the heteroarylcycloalkyl radical may be optionally substituted as defined above for a heteroaryl group.

"Heteroarylalkenyl" refers to a radical of the formula —$R_b R_f$ where $R_b$ is an alkenyl radical as defined above and $R_f$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"Hydroxyalkyl" refers to a radical of the formula —$R_a$—OH where $R_a$ is an alkyl radical as defined above. The hydroxy group may be attached to the alkyl radical on any carbon within the alkyl radical. The alkyl part of the hydroxyalkyl group may be optionally substituted as defined above for an alkyl group.

"$C_2$-$C_{12}$hydroxyalkyl" refers to a hydroxyalkyl radical as defined above containing two to twelve carbon atoms. The alkyl part of the $C_2$-$C_{12}$hydroxyalkyl radical may be optionally substituted as defined above for an alkyl group.

"$C_3$-$C_{12}$hydroxyalkyl" refers to a hydroxyalkyl radical as defined above containing three to twelve carbon atoms. The alkyl part of the $C_3$-$C_{12}$hydroxyalkyl radical may be optionally substituted as defined above for an alkyl group.

"$C_7$-$C_{12}$hydroxyalkyl" refers to a hydroxyalkyl radical as defined above containing seven to twelve carbon atoms. The alkyl part of the $C_7$-$C_{12}$hydroxyalkyl radical may be optionally substituted as defined above for an alkyl group.

"Hydroxyalkenyl" refers to a radical of the formula —$R_c$—OH where $R_c$ is an alkenyl radical as defined above. The hydroxy group may be attached to the alkenyl radical on any carbon within the alkenyl radical. The alkenyl part of the hydroxyalkenyl group may be optionally substituted as defined above for an alkenyl group.

"$C_2$-$C_{12}$hydroxyalkenyl" refers to a hydroxyalkenyl radical as defined above containing two to twelve carbon atoms. The alkenyl part of the $C_2$-$C_{12}$hydroxyalkenyl radical may be optionally substituted as defined above for an alkenyl group.

"$C_3$-$C_{12}$hydroxyalkenyl" refers to an hydroxyalkenyl radical as defined above containing three to twelve carbon atoms. The alkenyl part of the $C_3$-$C_{12}$hydroxyalkenyl radical may be optionally substituted as defined above for an alkenyl group.

"Hydroxyl-$C_1$-$C_6$-alkyl" refers to a radical of the formula —$R_h$—OH where $R_h$ is an unbranched alkyl radical having one to six carbons and the hydroxy radical is attached to the terminal carbon.

"Trihaloalkyl" refers to an alkyl radical, as defined above, that is substituted by three halo radicals, as defined above, e.g., trifluoromethyl. The alkyl part of the trihaloalkyl radical may be optionally substituted as defined above for an alkyl group.

"$C_1$-$C_6$trihaloalkyl" refers to a trihaloalkyl radical as defined above having one to six carbon atoms. The $C_1$-$C_6$trihaloalkyl may be optionally substituted as defined above for a trihaloalkyl group.

"Trihaloalkoxy" refers to a radical of the formula —$OR_g$ where $R_g$ is a trihaloalkyl group as defined above. The trihaloalkyl part of the trihaloalkoxy group may be optionally substituted as defined above for a trihaloalkyl group.

"$C_1$-$C_6$trihaloalkoxy" refers to a trihaloalkoxy radical as defined above having one to six carbon atoms. The $C_1$-$C_6$trihaloalkoxy group may be optionally substituted as defined above for a trihaloalkoxy group.

"A multi-ring structure" refers to a multicyclic ring system comprised of two to four rings wherein the rings are independently selected from cycloalkyl, aryl, heterocyclyl or heteroaryl as defined above. Each cycloalkyl may be optionally substituted as defined above for a cycloalkyl group. Each aryl may be optionally substituted as defined above for an aryl group. Each heterocyclyl may be optionally substituted as defined above for a heterocyclyl group. Each heteroaryl may be optionally substituted as defined above for a heteroaryl group. The rings may be attached to other through direct bonds or some or all of the rings may be fused to each other. Examples include, but are not limited to a cycloalkyl radical substituted by aryl group; a cycloalkyl group substituted by an aryl group, which, in turn, is substituted by another aryl group; and so forth.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like.

"Optonal" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of an SCD-mediated disease or condition in the mammal, preferably a human. The amount of a compound of the invention which constitutes a "therapeutically effective amount" will vary depending on the compound, the condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development; or (iii) relieving the disease or condition, i.e., causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The chemical naming protocol and structure diagrams used herein employ and rely the chemical naming features as utilized by Chemdraw version 7.0.1 (available from Cambridgesoft Corp., Cambridge, Mass.). For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms which are assumed to be bonded to sufficient hydrogen atoms to complete the valency.

As an example, a compound of formula (VIb), as set forth above in the Summary of the Invention, wherein x and y are each 1; $R^1$, $R^4$, $R^5$, $R^6$, $R^7$, $R^{7a}$, $R^8$, $R^{8a}$, $R^9$, $R^{9a}$, $R^{10}$ and $R^{10a}$ are each hydrogen; $R^2$ is 3-(4-fluoropheny)propyl and $R^3$ is 2-trifluoromethyl phenyl, i.e., a compound of the following formula:

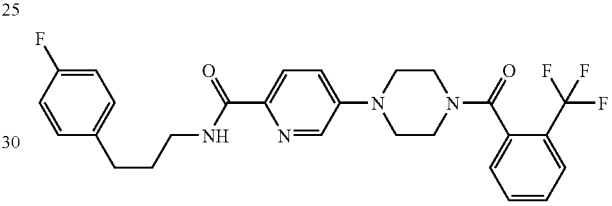

is named herein as 5-[4(2-Trifluoromethyl-benzoyl)-piperazin-1-yl]-pyridine-2-carboxylic acid [3-(4-fluoro-phenyl)-propyl]-amide.

Certain radical groups of the compounds of the invention are depicted herein as linkages between two parts of the compounds of the invention. For example, in the following formula (I):'

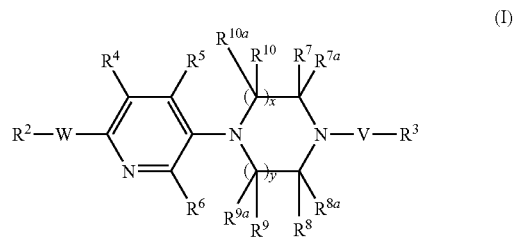

(I)

W is described, for example, as being —C(O)N($R^1$)— or —N($R^1$)C(O)N($R^1$)—; and V is described as —C(O)—. This description is meant to describe a W group attached to the $R^2$ group as follows: $R^2$—C(O)N($R^1$)— or $R^2$—N($R^1$)C(O)N($R^1$)—; and meant to describe a V group attached to the $R^3$ group as follows: —C(O)$R^3$. In other words, the description of the W and V linkage groups are meant to be read from left to right in view of formula (I) as depicted above.

Embodiments of the Invention

In one embodiment of the invention, compounds of formula (IIa), as set forth above in the Summary of the Invention, are directed to compounds wherein x and y are each 1; $R^1$ is hydrogen or $C_1$-$C_6$alkyl; $R^2$ is selected from the group consisting of $C_7$-$C_{12}$alkyl, $C_3$-$C_{12}$alkenyl, $C_7$-$C_{12}$hydroxyalkyl, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_3$-$C_{12}$heterocyclylalkyl, and $C_3$-$C_{12}$heteroarylalkyl; $R^3$ is selected from the group consisting of $C_3$-$C_{12}$alkyl, $C_3$-$C_{12}$alkenyl, $C_3$-$C_{12}$hydroxyalkyl, $C_3$-$C_{12}$hydroxyalkenyl, $C_3$-$C_{12}$alkoxy, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$ heteroaryl and $C_3$-$C_{12}$heteroarylalkyl; $R^4$, $R^5$ and $R^6$ are each hydrogen; and $R^7$, $R^{7a}$, $R^8$, $R^{8a}$, $R^9$, $R^{9a}$, $R^{10}$, and $R^{10a}$ are each hydrogen.

In another embodiment of the invention, compounds of formula (IIb), as set forth above in the Summary of the Invention, are directed to compounds wherein x and y are each 1; $R^1$ is hydrogen or $C_1$-$C_6$alkyl; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^2$)$_2$, —OC(O)$R^{12}$, —C(O)O$R^{12}$ and —S(O)$_2$N($R^{12}$)$_2$; $R^4$, $R^5$ and $R^6$ are each hydrogen; $R^7$, $R^{7a}$, $R^8$, $R^{8a}$, $R^9$, $R^{9a}$, $R^{10}$, and $R^{10a}$ are each hydrogen; and each $R^{12}$ is independently selected from hydrogen, $C_1$-$C_6$alkyl, $C_3$-$C_6$cycloalkyl, aryl or aralkyl.

One embodiment of this embodiment are compounds wherein $R^2$ is $C_7$-$C_{12}$aralkyl optionally substituted by one or more substituents selected from the group consisting of halo, $C_1$-$C_3$alkyl and $C_1$-$C_6$trihaloalkyl; and $R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

Another embodiment of this embodiment are compounds wherein $R^2$ is $C_1$-$C_{12}$alkyl or $C_2$-$C_{12}$alkenyl; and $R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

Another embodiment of this embodiment are compounds wherein $R^2$ is $C_3$-$C_{12}$heteroarylalkyl optionally substituted by one or more substituents selected from the group consisting of halo, $C_1$-$C_3$alkyl and $C_1$-$C_6$trihaloalkyl; and $R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

Another embodiment of this embodiment are compounds wherein $R^2$ is phenyl optionally substituted with one or more substituents selected from halo and $C_1$-$C_6$trihaloalkyl; and $R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

In another embodiment of the invention, compounds of formula (III), as set forth above in the Summary of the Invention, are directed to compounds wherein x and y are each 1; $V_a$ is —C(O)—; $R^1$ is hydrogen or $C_1$-$C_6$alkyl; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl; $R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; $R^4$, $R^5$ and $R^6$ are each hydrogen; and $R^7$, $R^{7a}$, $R^8$, $R^{8a}$, $R^9$, $R^{9a}$, $R^{10}$, and $R^{10a}$ are each hydrogen.

One embodiment of this embodiment are compounds wherein $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

One embodiment of this embodiment are compounds wherein $R^2$ is $C_1$-$C_{12}$alkyl or $C_2$-$C_{12}$alkenyl; and $R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

Another embodiment of this embodiment are compounds wherein $R^2$ is $C_7$-$C_{12}$aralkyl optionally substituted by one or more substituents selected from the group consisting of halo, $C_1$-$C_3$alkyl and $C_1$-$C_6$trihaloalkyl; and $R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

In another embodiment of the invention, compounds of formula (IV), as set forth above in the Summary of the Invention, are directed to compounds wherein x and y are each 1; $V_a$ is —C(O)—; each $R^1$ is independently hydrogen or $C_1$-$C_6$alkyl; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl; $R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; $R^4$, $R^5$ and $R^6$ are each hydrogen; and $R^7$, $R^{7a}$, $R^8$, $R^{8a}$, $R^9$, $R^{9a}$, $R^{10}$, and $R^{10}$a are each hydrogen.

One embodiment of this embodiment are compounds wherein $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

One embodiment of this embodiment are compounds wherein $R^2$ is $C_1$-$C_{12}$alkyl or $C_2$-$C_{12}$alkenyl; and $R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

Another embodiment of this embodiment are compounds wherein $R^2$ is $C_7$-$C_{12}$aralkyl optionally substituted by one or more substituents selected from the group consisting of halo, $C_1$-$C_3$alkyl and $C_1$-$C_6$trihaloalkyl; and $R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

In another embodiment of the invention, compounds of formula (V), as set forth above in the Summary of the Invention, are directed to compounds wherein x and y are each 1; $W_a$ is —O—; $V_a$ is —C(O)—; $R^1$ is hydrogen or $C_1$-$C_6$alkyl; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; $R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; $R^4$, $R^5$ and $R^6$ are each hydrogen; and $R^7$, $R^{7a}$, $R^8$, $R^{8a}$, $R^9$, $R^{9a}$, $R^{10}$, and $R^{10a}$ are each hydrogen.

One embodiment of this embodiment are compounds wherein $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

In another embodiment of the invention, compounds of formula (V), as set forth above in the Summary of the Invention, are directed to compounds wherein x and y are each 1; $W_a$ is —N($R^1$)—; $V_a$ is —C(O)—; $R^1$ is hydrogen or $C_1$-$C_6$alkyl; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; $R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; $R^4$, $R^5$ and $R^6$ are each hydrogen; and $R^7$, $R^{7a}$, $R^8$, $R^{8a}$, $R^9$, $R^{9a}$, $R^{10}$, and $R^{10a}$ are each hydrogen.

One embodiment of this embodiment are compounds wherein $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

In another embodiment of the invention, compounds of formula (V), as set forth above in the Summary of the Invention, are directed to compounds wherein x and y are each 1; $W_a$ is —S(O)$_t$— (where t is 0, 1 or 2); $V_a$ is —C(O)—; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; $R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; $R^4$, $R^5$ and $R^6$ are each hydrogen; and $R^7$, $R^{7a}$, $R^8$, $R^{8a}$, $R^9$, $R^{9a}$, $R^{10}$, and $R^{10a}$ are each hydrogen.

One embodiment of this embodiment are compounds wherein $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

In another embodiment of the invention, compounds of formula (VIa), as set forth above in the Summary of the Invention, are directed to compounds wherein x and y are each 1; $R^1$ is hydrogen or $C_1$-$C_6$alkyl; $R^2$ is selected from the group consisting of $C_7$-$C_{12}$alkyl, $C_3$-$C_{12}$alkenyl, $C_7$-$C_{12}$hydroxyalkyl, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_3$-$C_{12}$heterocyclylalkyl, and $C_3$-$C_{12}$heteroarylalkyl; $R^3$ is selected from the group consisting of $C_3$-$C_{12}$alkyl, $C_3$-$C_{12}$alkenyl, $C_3$-$C_{12}$hydroxyalkyl, $C_3$-$C_{12}$hydroxyalkenyl, $C_3$-$C_{12}$alkoxy, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_5$-$C_{12}$heteroaryl and $C_3$-$C_{12}$heteroarylalkyl; $R^4$, $R^5$ and $R^6$ are each hydrogen; and $R^7$, $R^{7a}$, $R^8$, $R^{8a}$, $R^9$, $R^{9a}$, $R^{10}$, and $R^{10a}$ are each hydrogen.

In another embodiment of the invention, compounds of formula (VIb), as set forth above in the Summary of the Invention, are directed to compounds wherein x and y are each 1; $R^1$ is hydrogen or $C_1$-$C_6$alkyl; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; $R^3$ is naphthyl or phenyl, each optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$ or —S(O)$_2$N($R^{12}$)$_2$; $R^4$, $R^5$ and $R^6$ are each hydrogen; $R^7$, $R^{7a}$, $R^8$, $R^{8a}$, $R^9$, $R^{9a}$, $R^{10}$, and $R^{10a}$ are each hydrogen; and each $R^{12}$ is independently selected from hydrogen, $C_1$-$C_6$alkyl, $C_3$-$C_6$cycloalkyl, aryl or aralkyl.

One embodiment of this embodiment are compounds wherein $R^2$ is $C_7$-$C_{12}$aralkyl optionally substituted by one or more substituents selected from the group consisting of halo, $C_1$-$C_3$alkyl and $C_1$-$C_6$trihaloalkyl; and $R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

Another embodiment of this embodiment are compounds wherein $R^2$ is $C_1$-$C_{12}$alkyl or $C_2$-$C_{12}$alkenyl; and $R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

Another embodiment of this embodiment are compounds wherein $R^2$ is $C_3$-$C_{12}$cycloalkyl or $C_4$-$C_{12}$cycloalkylalkyl; and $R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

Another embodiment of this embodiment are compounds wherein $R^2$ is $C_7$-$C_{12}$aralkyl optionally substituted by one or more substituents selected from the group consisting of halo, $C_1$-$C_3$alkyl and $C_1$-$C_6$trihaloalkyl; and $R^3$ is naphthyl optionally substituted by one or more substituents selected from the group consisting of halo, $C_1$-$C_6$alkyl, $C_1$-$C_6$trihaloalkyl and $C_1$-$C_6$trihaloalkoxy.

Another embodiment of this embodiment are compounds wherein $R^2$ is $C_3$-$C_{12}$heterocyclylalkyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$ or —S(O)$_2$N($R^{12}$)$_2$; $R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy; and each $R^{12}$ is independently selected from hydrogen, $C_1$-$C_6$alkyl, $C_3$-$C_6$cycloalkyl, aryl or aralkyl.

One embodiment of this embodiment are compounds wherein $R^2$ is 2-piperazinylethyl optionally substituted by —C(O)O$R^{12}$.

Specific embodiments of the compounds of the invention are disclosed herein in the following Reaction Schemes and Examples.

In another embodiment, the methods of the invention are directed to methods of treating a disease or condition mediated by stearoyl-CoA desaturase (SCD) in a mammal, wherein the method comprises administering to a mammal in need thereof a therapeutically effective amount of a compound of formulae (IIa), (IIb), (III), (IV), (V), (VIa) and (VIb).

In another embodiment of the pharmaceutical compositions of the invention are directed to pharmaceutical compositions comprising a pharmaceutically acceptable excipient and a therapeutically effective amount of a compound of formulae (IIa), (IIb), (III), (IV), (V), (VIa) and (VIb).

In another embodiment, the methods of the invention are directed towards the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, cardiovascular disease, diabetes, obesity, metabolic syndrome and the like by administering an effective amount of a compound of the invention.

The present invention also relates to pharmaceutical composition containing the compounds of the invention. In one embodiment, the invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

Utility and Testing of the Compounds of the Invention

The present invention relates to compounds, pharmaceutical compositions and methods of using the compounds and pharmaceutical compositions for the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, especially cardiovascular disease, diabetes, obesity, metabolic syndrome and the like, by administering to a patient in need of such treatment an effective amount of an SCD-modulating, especially inhibiting, agent.

In general, the present invention provides a method for treating a patient for, or protecting a patient from developing, a disease related to dyslipidemia and/or a disorder of lipid metabolism, wherein lipid levels in an animal, especially a human being, are outside the normal range (i.e., abnormal lipid level, such as elevated plasma lipid levels), especially levels higher than normal, preferably where said lipid is a fatty acid, such as a free or complexed fatty acid, triglycerides, phospholipids, or cholesterol, such as where LDL-cholesterol levels are elevated or HDL-cholesterol levels are reduced, or any combination of these, where said lipid-related condition or disease is an SCD-mediated disease or condition, comprising administering to an animal, such as a mammal, especially a human patient, a therapeutically effective amount of a compound of the invention or a pharmaceutical composition comprising a compound of the invention wherein the compound modulates the activity of SCD, preferably human SCD1.

The compounds of the invention modulate, preferably inhibit, the activity of human SCD enzymes, especially human SCD1.

The general value of the compounds of the invention in modulating, especially inhibiting, the activity of SCD can be determined using the assay described below in Example 5. Alternatively, the general value of the compounds in treating disorders and diseases may be established in industry standard animal models for demonstrating the efficacy of compounds in treating obesity, diabetes or elevated triglyceride or cholesterol levels or for improving glucose tolerance. Such models include Zucker obese fa/fa rats (available from Harlan Sprague Dawley, Inc. (Indianapolis, Ind.)), or the Zucker diabetic fatty rat (ZDF/GmiCrl-fa/fa) (available from Charles River Laboratories (Montréal, Quebec)).

The compounds of the instant invention are inhibitors of delta-9 desaturases and are useful for treating diseases and disorders in humans and other organisms, including all those human diseases and disorders which are the result of aberrant delta-9 desaturase biological activity or which may be ameliorated by modulation of delta-9 desaturase biological activity.

As defined herein, an SCD-mediated disease or condition includes but is not limited to a disease or condition which is, or is related to, cardiovascular disease, dyslipidemias (including but not limited to disorders of serum levels of triglycerides, hypertriglyceridemia, VLDL, HDL, LDL, fatty acid Desaturation Index (e.g. the ratio of 18:1/18:0 fatty acids, or other fatty acids, as defined elsewhere herein), cholesterol, and total cholesterol, hypercholesterolemia, as well as cholesterol disorders (including disorders characterized by defective reverse cholesterol transport), familial combined hyperlipidemia, coronary artery disease, atherosclerosis, heart disease, cerebrovascular disease (including but not limited to stroke, ischemic stroke and transient ischemic attack (TIA)), peripheral vascular disease, and ischemic retinopathy. In a preferred embodiment, compounds of the invention will, in a patient, increase HDL levels and/or decrease triglyceride levels and/or decrease LDL or non-HDL-cholesterol levels.

An SCD-mediated disease or condition also includes metabolic syndrome (including but not limited to dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia and anorexia), weight loss, body mass index and leptin related diseases. In a preferred embodiment, compounds of the invention will be used to treat diabetes mellitus and obesity.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaemia, hypercoagulability and/or microalbuminemia.

An SCD-mediated disease or condition also includes fatty liver, hepatic steatosis, hepatitis, non-alcoholic hepatitis, non-alcoholic steatohepatitis (NASH), alcoholic hepatitis, acute fatty liver, fatty liver of pregnancy, drug-induced hepatitis, erythrohepatic protoporphyria, iron overload disorders, hereditary hemochromatosis, hepatic fibrosis, hepatic cirrhosis, hepatoma and conditions related thereto.

An SCD-mediated disease or condition also includes but is not limited to a disease or condition which is, or is related to primary hypertriglyceridemia, or hypertriglyceridemia secondary to another disorder or disease, such as hyperlipoproteinemias, familial histiocytic reticulosis, lipoprotein lipase deficiency, apclipoprotein deficiency (such as ApoCII deficiency or ApoE deficiency), and the like, or hypertriglyceridemia of unknown or unspecified etiology.

An SCD-mediated disease or condition also includes a disorder of polyunsaturated fatty acid (PUFA) disorder, or a skin disorder, including but not limited to eczema, acne, psoriasis, keloid scar formation or prevention, diseases related to production or secretions from mucous membranes, such as monounsaturated fatty acids, wax esters, and the like.

An SCD-mediated disease or condition also includes inflammation, sinusitis, asthma, pancreatitis, osteoarthritis, rheumatoid arthritis, cystic fibrosis, and pre-menstrual syndrome.

An SCD-mediated disease or condition also includes but is not limited to a disease or condition which is, or is related to cancer, neoplasia, malignancy, metastases, tumours (benign or malignant), carcinogenesis, hepatomas and the like.

An SCD-mediated disease or condition also includes a condition where increasing lean body mass or lean muscle mass is desired, such as is desirable in enhancing performance through muscle building. Myopathies and lipid myopathies such as carnitine palmitoyltransferase deficiency (CPT I or CPT II) are also included herein. Such treatments are useful in humans and in animal husbandry, including for administration to bovine, porcine or avian domestic animals or any other animal to reduce triglyceride production and/or provide leaner meat products and/or healthier animals.

An SCD-mediated disease or condition also includes a disease or condition which is, or is related to, neurological diseases, psychiatric disorders, multiple sclerosis, eye diseases, and immune disorders.

An SCD-mediated disease or condition also includes a disease or condition which is, or is related to, viral diseases or infections including but not limited to all positive strand RNA viruses, coronaviruses, SARS virus, SARS-associated coronavirus, Togaviruses, Picornaviruses, Coxsackievirus, Yellow Fever virus, Flaviviridae, ALPHAVIRUS (TOGAVIRIDAE) including Rubella virus, Eastern equine encephalitis virus, Western equine encephalitis virus, Venezuelan equine encephalitis virus, Sindbis virus, Semliki forest virus, Chikungunya virus, O'nyong'nyong virus, Ross river virus, Mayaro virus, Alphaviruses; ASTROVIRIDAE including Astrovirus, Human Astroviruses; CALICIVIRIDAE including Vesicular exanthema of swine virus, Norwalk virus, Calicivirus, Bovine calicivirus, Pig calcivirus, Hepatitis E; CORONAVIRIDAE including Coronavirus, SARS virus, Avian infectious bronchitis virus, Bovine coronavirus, Canine coronavirus, Feline infectious peritonitis virus, Human coronavirus 299E, Human coronavirus OC43, Murine hepatitis virus, Porcine epidemic diarrhea virus, Porcine hemagglutinating encephalomyelitis virus, Porcine transmissible gastroenteritis virus, Rat coronavirus, Turkey coronavirus, Rabbit coronavirus, Berne virus, Breda virus; FLAVIVIRIDAE including Hepatitis C virus, West Nile virus, Yellow Fever virus, St. Louis encephalitis virus, Dengue Group, Hepatitis G virus, Japanese B encephalitis virus, Murray Valley encephalitis virus, Central European tick-borne encephalitis virus, Far Eastern tick-borne encephalitis virus, Kyasanur forest virus, Louping III virus, Powassan virus, Omsk hemorrhagic fever virus, Kumilinge virus, Absetarov anzalova hypr virus, Ilheus virus, Rocio encephalitis virus, Langat virus, Pestivirus, Bovine viral diarrhea, Hog cholera virus, Rio Bravo Group, Tyuleniy Group, Ntaya Group, Uganda S Group, Modoc Group; PICORNAVIRIDAE including Coxsackie A virus, Rhinovirus, Hepatitis A virus, Encephalomyocarditis virus, Mengovirus, ME virus, Human poliovirus 1, Coxsackie B; POTYVIRIDAE including Potyvirus, Rymovirus, Bymovirus. Additionally it can be a disease or infection caused by or linked to Hepatitis viruses, Hepatitis B virus, Hepatitis C virus, human immunodeficiency virus (HIV) and the like. Treatable viral infections include those where the virus employs an RNA intermediate as part of the replicative cycle (hepatitis or HIV); additionally it can be a disease or infection caused by or linked to RNA negative strand viruses such as influenza and parainfluenza viruses.

The compounds identified in the instant specification inhibit the desaturation of various fatty acids (such as the C9-C10 desaturation of stearoyl-CoA) which is accomplished by delta-9 desaturases, such as stearoyl-CoA desaturase 1 (SCD1). As such these compounds inhibit the formation of various fatty acids and downstream metabolites thereof. This may lead to an accumulation of stearoyl-CoA or palmitoyl-CoA and other upstream precursors of various fatty acids; which may possibly result in a negative feedback loop causing an overall change in fatty acid metabolism. Any of these consequences may ultimately be responsible for the overall therapeutic benefit provided by these compounds.

Typically, a successful SCD inhibitory therapeutic agent will meet some or all of the following criteria. Oral availability should be at or above 20%. Animal model efficacy is less than about 2 mg/Kg, 1 mg/Kg, or 0.5 mg/Kg and the target human dose is between 50 and 250 mg/70 Kg, although doses outside of this range may be acceptable, ("mg/Kg" means milligrams of compound per kilogram of body mass of the subject to whom it is being administered). The therapeutic index (or ratio of toxic dose to therapeutic dose) should be greater than 100. The potency (as expressed by $IC_{50}$ value) should be less than 10 μM, preferably below 1 μM and most preferably below 50 nM. The $IC_{50}$ ("Inhibitory Concentration—50%") is a measure of the amount of compound required to achieve 50% inhibition of SCD activity, over a specific time period, in an SCD biological activity assay. Any process for measuring the activity of SCD enzymes, preferably mouse or human SCD enzymes, may be utilized to assay the activity of the compounds useful in the methods of the invention in inhibiting said SCD activity. Compounds of the invention demonstrate an $IC_{50}$ in a 15 minute microsomal assay of preferably less than 10 μM, less than 5 μM, less than 2.5 µM, less than 1 µM, less than 750 nM, less than 500 nM, less than 250 nM, less than 100 nM, less than 50 nM, and most preferably less than 20 nM. The compound of the invention may show reversible inhibition (i.e., competitive inhibition) and preferably does not inhibit other iron binding proteins. The required dosage should preferably be no more than about once or twice a day or at meal times.

The identification of compounds of the invention as SCD inhibitors was readily accomplished using the SCD enzyme and microsomal assay procedure described in Brownlie et al, supra. When tested in this assay, compounds of the invention had less than 50% remaining SCD activity at 10 µM concentration of the test compound, preferably less than 40% remaining SCD activity at 10 µM concentration of the test compound, more preferably less than 30% remaining SCD activity at 10 µM concentration of the test compound, and even more preferably less than 20% remaining SCD activity at 10 µM concentration of the test compound, thereby demonstrating that the compounds of the invention are potent inhibitors of SCD activity.

These results provide the basis for analysis of the structure-activity relationship (SAR) between test compounds and SCD. Certain R groups tend to provide more potent inhibitory compounds. SAR analysis is one of the tools those skilled in the art may now employ to identify preferred embodiments of the compounds of the invention for use as therapeutic agents.

Other methods of testing the compounds disclosed herein are also readily available to those skilled in the art. Thus, in addition, said contacting may be accomplished in vivo. In one such embodiment, said contacting in step (a) is accomplished by administering said chemical agent to an animal afflicted with a triglyceride (TG)- or very low density lipoprotein (VLDL)-related disorder and subsequently detecting a change in plasma triglyceride level in said animal thereby identifying a therapeutic agent useful in treating a triglyceride (TG)- or very low density lipoprotein (VLDL)-related disorder. In such embodiment, the animal may be a human, such as a human patient afflicted with such a disorder and in need of treatment of said disorder.

In specific embodiments of such in vivo processes, said change in SCD1 activity in said animal is a decrease in activity, preferably wherein said SCD1 modulating agent does not substantially inhibit the biological activity of a delta-5 desaturase, delta-6 desaturase or fatty acid synthetase.

The model systems useful for compound evaluation may include, but are not limited to, the use of liver microsomes, such as from mice that have been maintained on a high carbohydrate diet, or from human donors, including persons suffering from obesity. Immortalized cell lines, such as HepG2 (from human liver), MCF-7 (from human breast cancer) and 3T3-L1 (from mouse adipocytes) may also be used. Primary cell lines, such as mouse primary hepatocytes, are also useful in testing the compounds of the invention. Where whole animals are used, mice used as a source of primary hepatocyte cells may also be used wherein the mice have been maintained on a high carbohydrate diet to increase SCD activity in mirocrosomes and/or to elevate plasma triglyceride levels (i.e., the 18:1/18:0 ratio); alternatively mice on a normal diet or mice with normal triglyceride levels may be used. Mouse models employing transgenic mice designed for hypertriglyceridemia are also available as is the mouse phenome database. Rabbits and hamsters are also useful as animal models, especially those expressing CETP (cholesteryl ester transfer protein).

Another suitable method for determining the in vivo efficacy of the compounds of the invention is to indirectly measure their impact on inhibition of SCD enzyme by measuring a subject's Desaturation Index after administration of the compound. "Desaturation Index" as employed in this specification means the ratio of the product over the substrate for the SCD enzyme as measured from a given tissue sample. This may be calculated using three different equations 18:1n–9/18:0 (oleic acid over stearic acid); 16:1n–7/16:0 (palmitoleic acid over palmitic acid); and/or 16:1n–7+18:1n–7/16:0 (measuring all reaction products of 16:0 desaturation over 16:0 substrate). Desaturation Index is primarily measured in liver or plasma triglycerides, but may also be measured in other selected lipid fractions from a variety of tissues. Desaturation Index, generally speaking, is a tool for plasma lipid profiling.

A number of human diseases and disorders are the result of aberrant SCD1 biological activity and may be ameliorated by modulation of SCD1 biological activity using the therapeutic agents of the invention.

Inhibition of SCD expression may also affect the fatty acid composition of membrane phospholipids, as well as production or levels of triglycerides and cholesterol esters. The fatty acid composition of phospholipids ultimately determines membrane fluidity, while the effects on the composition of triglycerides and cholesterol esters can affect lipoprotein metabolism and adiposity.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

Those skilled in the art know how to determine suitable doses of the compounds for use in treating the diseases and disorders contemplated herein. Therapeutic doses are generally identified through a dose ranging study in humans based on preliminary evidence derived from animal studies. Doses must be sufficient to result in a desired therapeutic benefit without causing unwanted side-effects for the patient. The preferred dosage range for an animal is 0.001 mg/Kg to 10,000 mg/Kg, including 0.5 mg/Kg, 1.0 mg/Kg and 2.0 mg/Kg, though doses outside this range may be acceptable. The dosing schedule may be once or twice per day, although more often or less often may be satisfactory.

Those skilled in the art are also familiar with determining administration methods (oral, intravenous, inhalation, subcutaneous, etc.), dosage forms, suitable pharmaceutical excipients and other matters relevant to the delivery of the compounds to a subject in need thereof.

In an alternative use of the invention, the compounds of the invention can be used in in vitro or in vivo studies as exemplary agents for comparative purposes to find other compounds also useful in treatment of, or protection from, the various diseases disclosed herein.

Preparation of the Compounds of the Invention

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyidimethylsilyl, t-butyidiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein.

The use of protecting groups is described in detail in Green, T.W. and P.G.M. Wutz, *Protective Groups in Organic Synthesis* (1999), 3rd Ed., Wiley. The protecting group may also be a polymer resin such as a Wang resin or a 2-chlorotritylchloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following Reaction Schemes illustrate methods to make compounds of this invention. It is understood that one of those skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention. $R^1$, $R^2$, $R^3$, $R^4$, $R^5$, $R^6$, $R^7$, $R^{7a}$, $R^8$, $R^{8a}$, $R^9$, $R^{9a}$, $R^{10}$, $R^{10a}$ and V are defined as in the Specification unless specifically defined otherwise. X is selected from Cl or Br. PG represents a protecting group such as BOC, benzyl group and the like.

In general, the compounds of formula (I) of the invention where W is —C(O)N($R^1$)— and V is —C(O)—, —S(O)$_2$— or —C($R^{11}$)H— can be synthesized following the general procedure as described in Reaction Scheme 1.

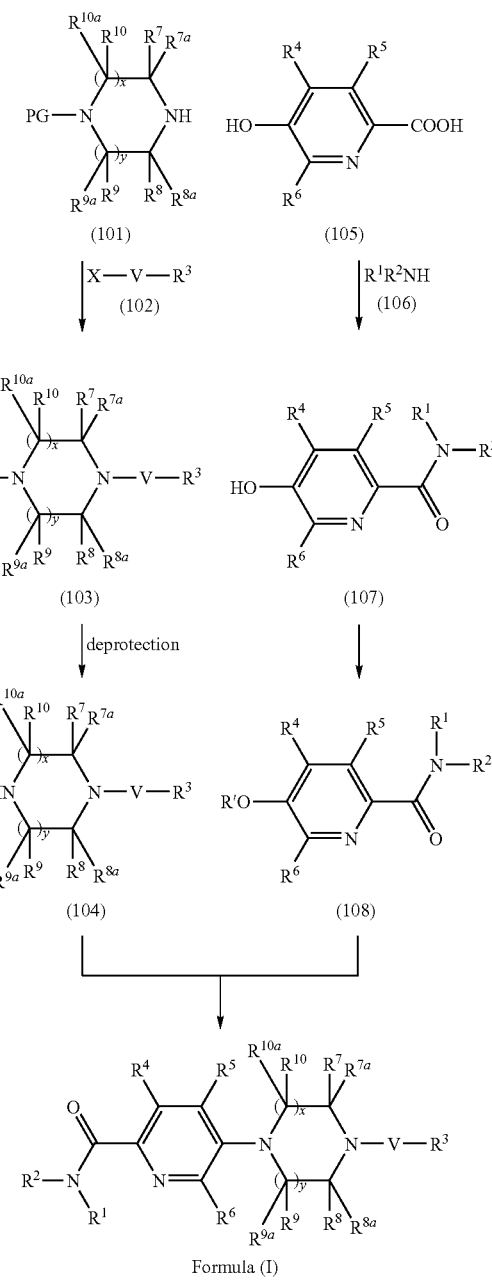

The starting materials for the above reaction scheme are commercially available or can be prepared according to methods known to one skilled in the art or by methods disclosed herein. In general, the compounds of the invention are prepared in the above reaction scheme as follows:

Compound (103): To a stirred solution of a compound of formula (101) (1 equivalent) in a solvent, such as dichloromethane, chloroform or toluene, but not limited to, at 0° C. in the presence of a base such as diisopropylethylamine, is added a solution of a compound of formula 102 (1 equivalent). The resulting mixture is stirred at ambient temperature for 8-24 h. The reaction is quenched with water. The organic phase is washed with water, dried over a drying agent such as anhydrous $Na_2SO_4$, filtered and concentrated in vacuo to yield compound (103).

Compound (104): A solution of compound of formula of (103) obtained above is dissolved in an adequate solvent and the protection group PG is removed under standard deprotection conditions such as hydrolysis or hydrogenation to obtain the amine of formula (104).

Compound (107): To a solution of 5-hydroxypyridine-2-carboxylic acid (1 equivalent) in a solvent such as dichloromethane, chloroform or toluene, is added a base such as triethylamine, diisopropylethylamine, followed by 1-hydroxybenzotriazole monohydrate (1 equivalent) and a coupling agent (1 equivalent) such as EDCl. The resulting mixture is stirred for 15-60 min and the amine of formula (106) (1 equivalent) is added. After stirring for 18-24 hours, the reaction mixture is diluted with dichloromethane, washed with water, dried over anhydrous $Na_2SO_4$, filtered and concentrated in vacuo. Purification by flash chromatography yields compound (107).

Compound (108): To a solution of compound of formula (107) obtained above (1 equivalent) at 0° C. in a solvent such as dichloromethane is added triethylamine (1.5 to 2.5 equivalent) followed by dropwise addition of a solution of trifluoromethanesulfonic anhydride (1.1 to 1.5 equivalent) in a solvent such as dichloromethane. The resulting mixture is stirred at 0° C. for 3-8 h and then quenched with water. The organic layer is separated, dried over anhydrous $MgSO_4$, filtered and concentrated in vacuo. Purification by flash column chromatography affords compound (108).

Compound of Formula (I): This compound is obtained using Buchwald reaction. In general, a flask under argon atmosphere is charged with a base such as cesium carbonate or potassium carbonate, palladium catalyst, such as palladium diacetate and a ligand such as BINAP. A solution of compound (108) and compound (104) in toluene is added via syringe. The reaction mixture is then heated at 100° C. for 26 h, cooled to ambient temperature, diluted with toluene, filtered and concentrated in vacuo. The crude product was purified via flash column chromatography affords compound of Formula (I).

Alternatively, the compounds of formula (I) of the invention where W is —C(O)NH— and V is —C(O)—, —S(O)$_2$— or —C(R$^{11}$)H— can be synthesized following the general procedure as described in Reaction Scheme 2.

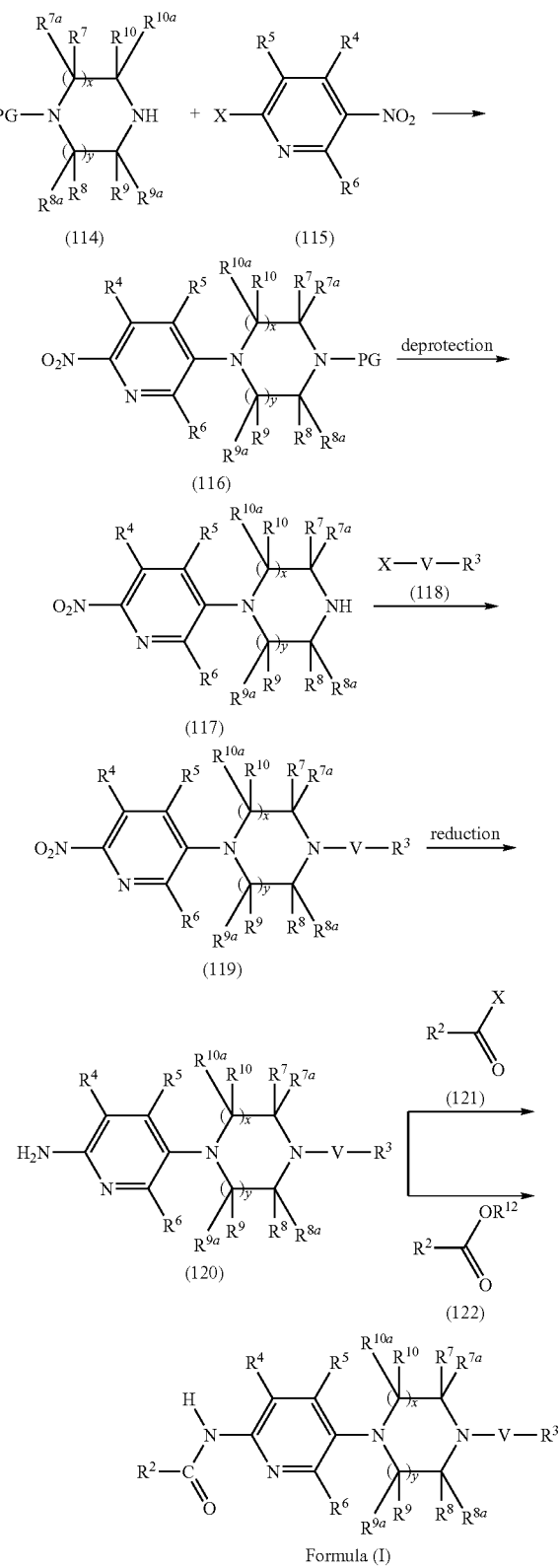

The starting materials for the above reaction scheme are commercially available or can be prepared according to methods known to one skilled in the art or by methods disclosed herein. In general, the compounds of the invention are prepared in the above reaction scheme as follows:

Compound 116. To a stirred solution of the amine of formula (114) (1 equivalent) in a solvent such as dichloromethane or toluene is added the solution of a chloride of formula (115) (1 equivalent) in a solvent such as dichloromethane or toluene in the presence of a base such as triethylamine or Hunigs base. The resulting mixture is stirred at ambient temperature for an adequate time period and then quenched with water. The organic phase is washed with $H_2O$, brine, dried over and then concentrated in vacuo to afford the product of formula (116).

Compound 117. A solution of compound of formula of (116) obtained above is dissolved in an adequate solvent and the protection group PG is removed under standard deprotection conditions such as hydrolysis or hydrogenation to obtain the amine of formula (117).

Compound 119. The mixture of a pyridine compound of formula (117) (1 equivalent) and the compound of formula (118) (1.5 equivalent) in an adequate solvent is heated at reflux for 4-24 hours. To the reaction mixture is added a basic solution such as NaOH solution. The aqueous layer is extracted by an organic solvent such as dichloromethane or ethyl acetate. The combined organic phase is dried, then evaporated to dryness. The crude compound is purified by column chromatography or crystallization to afford the compound of formula (119).

Compound 120. The nitro compound of formula (119) can be reduced to the corresponding amine compound of formula (120) using a standard hydrogenation process known to one skilled in the art.

Compound of formula (I):

Method A: To a stirred solution of compound of formula (120) (1 equivalent) in a solvent such as dichloromethane, acetonitrile or toluene is added the solution of a compound of formula (121) (1 equivalent) in the presence of a base such as triethylamine or Hunigs base (1 equivalent) at 0° C. The resulting mixture is stirred at ambient temperature for 8-24 hours and then quenched with water. The organic phase is washed with $H_2O$, brine, dried and then concentrated in vacuo to afford the compound of formula (I) where W is —C(O)NH— and V is —C(O)—, —S(O)$_2$— or —C(R$^{11}$)H—.

Method B: To a solution of the compound of formula (122) (1 equivalent) in a solvent such as dichloromethane, toluene or THF is added a base such as triethylamine or Hunigs base (2.5 equivalent), followed by the addition of a coupling agent such as (3-dimethylaminopropyl)ethyl carbodiimide (1.1 equivalent). The resulting mixture is stirred for 15 minutes to an hour and an amine of formula (120) (1.1 equivalent) is added. The mixture is stirred at ambient temperature for 8-24 hours, then washed with water, dried and concentrated in vacuo. Purification by column chromatography or crystallization from a suitable solvent affords the compound of formula (I) where W is —C(O)NH— and V is —C(O)—, —S(O)$_2$— or —C(R$^{11}$)H—.

Alternatively, the compounds of formula (I) of the invention where W is —NHC(O)NH— and V is —C(O)—, —S(O)$_2$— or —C(R$^{11}$)H— can be synthesized following the general procedure as described in Reaction Scheme 3.

REACTION SCHEME 3

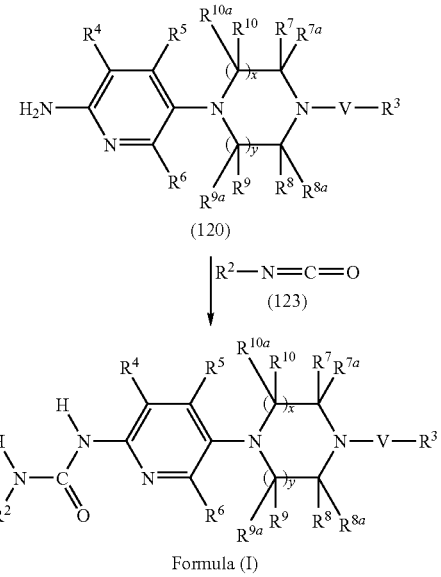

The starting materials for the above reaction scheme are commercially available or can be prepared according to methods known to one skilled in the art or by methods disclosed herein. In general, the compounds of the invention are prepared in the above reaction scheme as follows:

Compound of formula (I). To a stirred solution of the compound of formula (120) (1 equivalent) in an anhydrous solvent such as dimethylformamide is added an isocyanate of formula (123) (3 equivalent), and the mixture is then heated to 60-80° C. for 4-24 hours. The mixture is concentrated in vacuo. Purification of the crude product by column chromatography or crystallization from a suitable solvent affords the compound of formula (I) where W is —NHC(O)NH— and V is —C(O)—, —S(O)$_2$— or —C(R$^{11}$)H—.

Alternatively, the compounds of formula (I) of the invention where W is —S(O)$_2$NH— and V is —C(O)—, —S(O)$_2$— or —C(R$^{11}$)H— can be synthesized following the general procedure as described in Reaction Scheme 4.

REACTION SCHEME 4

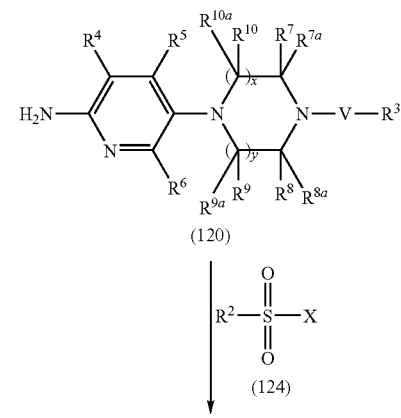

-continued

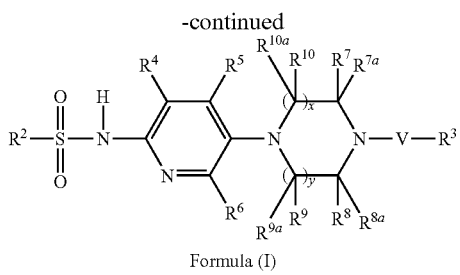

Formula (I)

The starting materials for the above reaction scheme are commercially available or can be prepared according to methods known to one skilled in the art or by methods disclosed herein. In general, the compounds of the invention are prepared in the above reaction scheme as follows:

Compound of formula (I): To a solution of compound of formula (118) (1 equivalent) in a solvent such as dichloromethane, acetonitrile or toluene is added slowly the solution of compound of formula (124) (1 equivalent) at 0° C. The resulting mixture is stirred at ambient temperature for 8-24 hours and then quenched with water. After removal of solvent, the product was purified by chromatography to afford the compound of formula (I) where W is —S(O)$_2$NH— and V is —C(O)—, —S(O)$_2$— or —C(R$^{11}$)H—.

Preparation 1

Synthesis of PIPERAZIN-1-YL-(2-TRIFLUOROMETHYLPHENYL)METHANONE

A. To a stirred solution of 1-Boc-piperazine (0.50 g, 2.7 mmol) and diisopropylethylamine (1.75 g, 13.5 mmol) in dichloromethane at 0° C. was added a solution of 2-trifluoromethylbenzoyl chloride (0.626 g, 3.0 mmol). The resulting mixture was stirred at room temperature for 20 h and then quenched with water (25 mL). The organic phase was washed with water, dried over anhydrous Na$_2$SO$_4$, filtered and concentrated in vacuo to yield 4-(2-trifluoromethylbenzoyl)piperazine-1-carboxylic acid tert-butyl ester as a pale brown oil (0.948 g, 98% yield). $^1$H NMR (300 MHz, CDCl$_3$) δ 7.69, 7.54, 7.30, 3.77, 3.51, 3.33, 3.14, 1.45.

B. A solution of 4-(2-trifluoromethylbenzoyl)piperazine-1-carboxylic acid tert-butyl ester (0.948 g, 2.65 mmol) in 50 mL of a 1:4 mixture of trifluoroacetic acid and dichloromethane was stirred at room temperature for 20 h. After concentration in vacuo, the residue was dissolved in dichloromethane (100 mL) and washed with 1 N NaOH (10 mL), water (15 mL), and brine (15 mL). The organic phase was dried over anhydrous Na$_2$SO$_4$, filtered and concentrated in vacuo to yield the title compound as a light brown oil (0.657 g, 2.54 mmol). $^1$H NMR (300 MHz, CDCl$_3$) δ 7.69, 7.54, 7.30, 3.78, 3.15, 2.94, 2.76. MS (ES+) m/z 259.3 (M+1).

Preparation 2

Synthesis of TRIFLUOROMETHANESULFONIC ACID 6-(3-PHENYLPROPYLCARBAMOYL)PYRIDIN-3-YL ESTER A. To a solution of 5-hydroxypyridine-2-carboxylic acid (0.103 g, 0.74 mmol) in dichloromethane was added diisopropylethylamine (0.279 mL, 1.6 mmol), followed by 1-hydroxybenzotriazole monohydrate (0.012 g, 0.8 mmol) and EDCI (0.153 g, 0.8 mmol). The resulting mixture was stirred for 15 minutes and 3-phenyl-1-propylamine (0.108 g, 0.8 mmol) was added. After stirring for 22 h, the reaction mixture was diluted with dichloromethane (80 mL), washed with water, dried over anhydrous Na$_2$SO$_4$ and concentrated in vacuo. Purification by column chromatography afforded 5-hydroxypyridine-2-carboxylic acid (3-phenylpropyl) amide as white crystals (0.116 g, 61% yield). MS (ES+) m/z 257.2 (M+1).

B. To a solution of 5-hydroxypyridine-2-carboxylic acid (3-phenylpropyl)amide obtained above (0.097 g, 0.378 mmol) at 0° C. in dichloromethane (5 mL) was added triethylamine (0.079 mL, 0.567 mmol) followed by dropwise addition of a solution of trifluoromethanesulfonic anhydride (0.077 mL, 0.454 mmol) in dichloromethane (2 mL). The mixture was stirred at 0° C. for 5 h and quenched with water (25 mL). The organic phase was separated, dried over anhydrous MgSO$_4$, filtered and concentrated in vacuo. The residue was purified by column chromatography and the title compounds was obtained as a clear oil (0.124 g, 84% yield). MS (ES+) m/z 389.3 (M+1).

Preparation 3

Synthesis of [4-(6-AMINOPYRIDIN-3-YL)PIPERAZIN-1-YL]-(2-TRIFLUOROMETHYLPHENYL) METHANONE A. To a solution of 1-Boc-piperazine (0.242 g, 1.3 mmol) in DMSO (5 mL) was added tetrabutylammonium iodide (0.037 g, 0.1 mmol), K$_2$CO$_3$ (0.207 g, 1.5 mmol), and 5-bromo-2-nitropyridine (0.202 g, 1.0 mmol). The resulting mixture was heated at 132° C. for 95 h and then cooled to room temperature, and diluted with ethyl acetate (50 mL). The organic layer was washed with brine, dried over anhydrous MgSO$_4$, filtered and concentrated in vacuo to give crude product. The desired product was obtained as a yellow solid (0.082 g, 27% yield) after further wash with cold ether and dried in vacuo. MS (ES+) m/z 309.5 (M+1).

B. A solution of 4-(6-nitropyridin-3-yl)piperazine-1-carboxylic acid tert-butyl ester obtaine above (0.821 g, 0.27 mmol) in 10 mL of a 1:4 mixture of trifluoroacetic acid and dichloromethane was stirred at room temperature for 2 h. The mixture was concentrated in vacuo to yield 1-(6-nitropyridin-3-yl)piperazine as a brown oil (0.086 g, TFA salt, 100% yield). MS (ES+) m/z 209.4 (M+1).

C. To a solution of 1-(6-nitropyridin-3-yl)piperazine obtained above (0.086 g, 0.41 mmol) and diisopropylethylamine (0.16 mL, 0.9 mmol) in dichloromethane (2 mL) at 0° C. was added 2-trifluoromethylbenzoyl chloride (0.094 g, 0.45 mmol) in dichloromethane (2 mL). The resulting mixture was stirred at room temperature for 4 h and then quenched with MeOH (0.5 mL). The organic layer was diluted with dichloromethane (5 mL), washed with brine, dried over anhydrous MgSO$_4$, filtered and concentrated in vavuo to afford [4-(6-nitropyridin-3-yl)piperazin-1-yl]-(2-trifluoromethylphenyl)methanone as a yellow solid (0.089 g, 70% yield). MS (ES+) m/z 381.3 (M+1).

D. To a solution of [4-(6-nitropyridin-3-yl)piperazin-1-yl]-(2-trifluoromethylphenyl)-methanone (0.089 g, 0.23 mmol) in 1:1 THF:MeOH (5 mL) was added 10% Pd/C (0.051 g). The resulting mixture was stirred under hydrogen atmosphere at 25° C. for 4 h. After filtering through a celite cake, the solution was concentrated in vacuo and yielded the title compound as a light yellow solid (0.039 g, 49% yield). MS (ES+) m/z 351.3.

EXAMPLE 1

Synthesis of 5-[4-(2-TRIFLUOROMETHYLBEN-ZOYL)PIPERAZIN-1-YL]PYRIDINE-2-CAR-BOXYLIC ACID (3-PHENYLPROPYL)AMIDE A 50-mL flask was charged with cesium carbonate (0.078 g, 0.238 mmol), palladium diacetate (0.0019 g, 0.0085 mmol) and BINAP (0.0079 g, 0.013 mmol) and flushed with argon for 30 minutes. A solution of trifluoromethanesulfonic acid 6-(3-phenylpropylcarbamoyl)pyridin-3-yl ester (0.066 g, 0.17 mmol) and piperazin-1-yl-(2-trifluoromethylphenyl) methanone (0.053 g, 0.20 mmol) in toluene (2 mL) was added via syringe. The reaction mixture was heated at 100 C for 26 h, cooled to room temperature, diluted with toluene (20 mL), filtered and concentrated in vacuo. The crude product was purified by column chromatography to afford the title compound as a white solid (0.011 g, 13% yield). $^1$H NMR (300 MHz, CDCl$_3$) δ 8.15, 8.04, 7.85, 7.74, 7.50-7.65, 7.36, 7.30-7.10, 3.90-4.10, 3.55-3.30, 3.22, 2.72, 1.96. MS (ES+) m/z 497.4 (M+1).

EXAMPLE 1.1

The following compounds were synthesized by the similar procedure as described in Example 1:

5-[4-(2-Trifluoromethylbenzoyl)piperazin-1-yl]pyridine-2-carboxylic acid (3-methylbutyl)amide; $^1$H NMR (CDCl$_3$) δ 8.15-8.14, 8.06, 7,76-7.72, 7.63-7.58, 7.37-7.34, 7.24-7.19, 4.1-3.95, 3.49-3.36, 3.23-3.19, 1.73-1.66, 1.55-1.53, 0.96; MS (ES+) m/z 449 (M+1);

5-[4(2-Trifluoromethylbenzoyl)piperazin-1-yl]pyridine-2-carboxylic acid hexylamide; $^1$H NMR (CDCl$_3$) δ 8.24, 8.15, 8.11, 7.78, 7.65, 7.60, 7.39, 3.89-4.19, 3.32-3.60, 3.30, 1.61, 1.19-1.50, 0.88; MS (ES+) m/z 463 (M+1);

5-[4-(2-Trifluoromethylbenzoyl)piperazin-1-yl]pyridine-2-carboxylic acid pentylamide; $^1$H NMR (CDCl$_3$) δ 8.21, 8.13, 8.05, 7.75, 7.65, 7.60, 7.39, 7.32, 3.89-4.14, 3.46, 3.40, 3.30, 1.65, 1.35, 1.25, 0.90; MS (ES+) m/z 449 (M+1);

5-[4-(2-Trifluoromethylbenzoyl)piperazin-1-yl]pyridine-2-carboxylic acid phenethylamide; $^1$H NMR (CDCl$_3$) δ 8.21, 8.15, 8.12, 7.78, 7.61, 7.58, 7.38, 7.32, 7.24, 3.89-4.15, 3.71, 3.49, 3.40, 3.29, 2.91, 3.32-3.60, 3.30, 1.61, 1.19-1.50, 0.88; MS (ES+) m/z 483 (M+1);

5-[4-(Naphthalene-1-carbonyl)piperazin-1-yl]pyridine-2-carboxylic acid (3-phenylpropyl)-amide; $^1$H NMR (CDCl$_3$) δ 8.13-8.12, 8.05-8.02, 7.91-7.82, 7.55-7.42, 7.297.13, 4.17-4.07, 3.51-3.37, 3.18-3.13, 2.73-2.68, 1.99-1.89; MS (ES+) m/z 479.5 (M+1);

5-[4-(Naphthalene-1-carbonyl)piperazin-1-yl]pyridine-2-carboxylic acid (3-methylbutyl)-amide; $^1$H NMR (CDCl$_3$) δ 8.19, 8.08, 7.87-8.00, 7.82, 7.41-7.61, 7.29, 4.01-4.28, 3.08-3.73, 1.60-1.72, 1.55, 0.91; MS (ES+) m/z 431 (M+1);

5-[4-(Naphthalene-1-carbonyl)piperazin-1-yl]pyridine-2-carboxylic acid hexylamide; $^1$H NMR (CDCl$_3$) δ 8.23, 8.13, 8.08, 7.85-8.00, 7.85, 7.45-7.60, 7.32, 4.02-4.28, 3.59, 3.31-3.50, 3.22, 1.75, 1.19-1.46, 0.89; MS (ES+) m/z 445 (M+1);

5-[4-(Naphthalene-1-carbonyl)piperazin-1-yl]pyridine-2-carboxylic acid phenethylamide; $^1$H NMR (CDCl$_3$) δ 8.0-8.35, 7.95, 7.80, 7.54, 7.49, 7.30, 7.24, 4.01-4.29, 3.75, 3.51, 3.41, 3.22, 2.94; MS (ES+) m/z 465 (M+1);

5-[4-(Naphthalene-1-carbonyl)piperazin-1-yl]pyridine-2-carboxylic acid pentylamide; $^1$H NMR (CDCl$_3$) δ 8.29, 8.10-8.25, 7.95, 7.81, 7.50-7.63, 7.50, 7.39, 4.06-4.30, 3.60, 3.45, 3.25, 1.64, 1.35, 1.25, 0.90; MS (ES+) m/z 431 (M+1);

5-[4-(2-Trifluoromethylbenzoyl)piperazin-1-yl]pyridine-2-carboxylic acid [2-(4-fluoro-phenyl)ethyl]amide; $^1$H NMR (CDCl$_3$) δ 8.11, 8.04, 7.85, 7.74-7.71, 7.62-7.52, 7.36-7.34, 7.23-7.17, 6.99-6.94, 4.06-3.9, 3.71-3.61, 3.41-3.35, 3.24-3.19, 2.89; MS (ES+) m/z 501.2 (M+1);

5-[4-(2-Trifluoromethylbenzoyl)piperazin-1-yl]pyridine-2-carboxylic acid [3-(4-fluorophenyl)propyl]amide; $^1$H NMR: (CDCl$_3$) δ 8.14-8.13, 8.06-8.03, 7.82, 7.74-7.72, 7.64-7.55, 7.36-7.34, 7.25-7.2, 7.19-7.11, 6.97-6.91, 4.04-3.94, 3.5-3.36, 3.23-3.19, 2.71-2.65, 1,98-1.9; MS (ES+) m/z 515.5 (M+1);

5-[4-(2-Trifluoromethylbenzoyl)piperazin-1-yl]pyridine-2-carboxylic acid (3-cyclohexylpropyl)amide; $^1$H NMR (CDCl$_3$) δ 8.14, 8.05, 7.79, 7.73, 7.62, 7.55, 7.35, 7.21, 3.86-4.11, 3.32-3.45, 3.21, 1.50-1.75, 1,08-1.37, 0.78-0.96; MS (ES+) m/z 502 (M);

4-[2-({5-[4-(2-Trifluoromethylbenzoyl)piperazin-1-yl]pyridine-2-carbonyl}amino)ethyl]-piperazine-1-carboxylic acid tert-butyl ester; $^1$H NMR: (CDCl$_3$) δ 8.17-8.16, 8.1-8.03, 7.74-7.72, 7.62-7.55, 7.37-7.34, 7.25-7.19, 4.04-3.94, 3.59-3.53, 3.46-3.35, 3.23-3.19, 2.62-2.58, 2.47-2.44, 1.64, 1.46, 1.25; MS (ES+) m/z 591.5 (M+1);

5-[4-(4-Fluoro-2-trifluoromethylbenzoyl)piperazin-1-yl]pyridine-2-carboxylic acid (3-methylbutyl)amide;

5-[4-(5-Fluoro-2-trifluoromethylbenzoyl)piperazin-1-yl]pyridine-2-carboxylic acid (3-methylbutyl)amide;

5-[4-(6-Trifluoromethylbenzoyl)piperazin-1-yl]pyridine-2-carboxylic acid (2-cyclohexylethyl)amide;

5-[4-(2-Trifluoromethylbenzoyl)piperazin-1-yl]pyridine-2-carboxylic acid 4-trifluoromethyl-benzylamide;

5-[4-(2-Trifluoromethylbenzoyl)piperazin-1-yl]pyridine-2-carboxylic acid [3-(4-trifluoromethylphenyl)propyl]amide;

5-[4-(2-Trifluoromethylbenzoyl)piperazin-1-yl]pyridine-2-carboxylic acid [2-(4-trifluoromethylphenyl)ethyl]amide;

5-[4-(2-Trifluoromethylbenzoyl)piperazin-1-yl]pyridine-2-carboxylic acid cyclohexylmethylamide; and 4-Fluoro-N-{5-[4-(2-trifluoromethylbenzoyl)piperazin-1-yl]pyridin-2-yl}benzamide.

EXAMPLE 2

Synthesis of 4-PHENYL-N-{5-[4-(2-TRIFLUO-ROMETHYLBENZOYL)PIPERAZIN-1-YL]-PY-RIDIN-2-YL}BUTYRAMIDE To a solution of [4-(6-aminopyridin-3-yl)piperazin-1-yl]-(2-trifluoromethylphenyl)-methanone (0.035 g, 0.10 mmol) in dichloromethane was added diisopropylethylamine (0.084 mL, 0.48 mmol), followed by 1-hydroxybenzotriazole monohydrate (0.018 g, 0.12 mmol), EDCI (0.023 g, 0.12 mmol) and DMAP (0.015 g, 0.12 mmol). The resulting mixture was stirred for 15 minutes and 3-phenyl-1-propylamine (0.020 g, 0.12 mmol) was added. After stirring for 18 h, the reaction mixture was diluted with ethyl acetate, washed with brine, dried over anhydrous MgSO$_4$, filtered and concentrated in vacuo. Purification by preparative thin layer chromatography afforded the title compound as a pale white solid (6.2 mg, 12.5% yield). $^1$H NMR(300 MHz, CDCl$_3$) δ 8.12, 7.97, 7.87, 7.72, 7.59, 7.34, 7.10-7.29, 3.98, 3.34, 3.22, 3.02, 2.70, 2.37, 2.08. MS (ES+) m/z 497.2 (M+1).

EXAMPLE 2.1

The following compounds were synthesized by the similar procedure as described in Example 2:

3-Pyridin-3-yl-N-{5-[4-(2-trifluoromethylbenzoyl)piperazin-1-yl]pyridin-2-yl}propionamide; $^1$H NMR(300 MHz, CDCl$_3$) δ 8.49-8.43 (m, 2H), 8.07 (d, 1H), 7.88 (d, 1H), 7.73-7.70 (m, 2H), 7.61-7.53 (m, 3H), 7.33-7.18 (m, 3H), 4.00-3.94 (m, 2H), 3.32 (t, 2H), 3.21 (t, 2H), 3.07-3.01 (m, 4H), 2.71 (t, 2H); MS (ES+) m/z 484.2 (M+1);

3-Phenyl-N-{5-[4-(2-trifluoromethylbenzoyl)piperazin-1-yl]pyridin-2-yl}propionamide; $^1$H NMR (300 MHz, CDCl$_3$) δ 8.12 (d, 1H), 7.86 (d, 1H), 7.73 (d, 1H), 7.61-7.53 (m, 2H), 7.35-7.17 (m, 6H), 3.99-3.94 (m, 2H), 3.33 (t, 2H), 3.19 (t, 2H), 3.06-2.98 (m, 4H), 2.70-2.64 (m, 2H); MS (ES+) m/z 483.1 (M+1);

Hexanoic acid {5-[4(2-trifluoromethylbenzoyl)piperazin-1-yl]pyridin-2-yl}amide; $^1$H NMR (300 MHz, CDCl$_3$) δ 8.12-7.65 (m, 5H), 7.55-7.40 (m, 2H), 4.08-3.96(m, 1H), 3.92-3.85 (m, 1H), 3.70-3.40 (m, 4H), 3.15-3.02 (m, 2H), 1.75-1.65 (m, 2H), 1.32-1.48 (m, 4H), 9.29 (t, 3H); MS (ES+) m/z 449.3 (M+1);

Heptanoic acid {5-[4-(2-trifluoromethylbenzoyl)piperazin-1-yl]pyridin-2-yl}amide; $^1$H NMR (300 MHz, CDCl$_3$) δ 8.60 (d, 1H), 7.76-7.57 (m, 5H), 7.35 (d, 1H), 4.08-3.92 (m, 2H), 3.40-3.27 (m, 4H), 3.10-3.06 (m, 2H), 2.51 (t, 2H), 1.73-1.66 (m, 2H), 1.40-1.26 (m, 8H0, 0.89 (t, 3H). MS (ES+) m/z 463.4 (M+1);

4-Methylpentanoic acid {5-[4(2-trifluoromethylbenzoyl)piperazin-1-yl]pyridin-2-yl}amide; $^1$H NMR (CDCl$_3$) δ 8.0-7.96, 7.83-7.8, 7.78-7.65, 7.53-7.5, 4.89, 3.96-3.93, 3.41-3.29, 3.23-3.19, 2.53-2.48, 1.65-1.6, 0.96. MS (ES+) m/z 449.4 (M+1);

3-(4Fluorophenyl)-N-{5-[4-(2-trifluoromethylbenzoyl)piperazin-1-yl]pyridin-2-yl}-propionamide; and 4(4-Fluorophenyl)-N-{5-[4-(2-trifluoromethylbenzoyl)piperazin-1-yl]pyridin-2-yl}-butyramide.

EXAMPLE 3

Synthesis of 1-BENZYL-3-{5-[4(2-TRIFLUOROMETHYLBENZOYL)PIPERAZIN-1-YL]PYRIDIN-2-YL}UREA To a solution of [4-(6-aminopyridin-3-yl)piperazin-1-yl]-(2-trifluoromethylphenyl)-methanone (0.035 g, 0.12 mmol) in dichloromethane (3 mL) was added benzylisocyanate (0.4 mL, 0.3 mmol). After stirring for 66 h, dichloromethane was removed in vacuo and the residue was diluted with ethyl acetate (20 mL). The organic phase was washed with brine, dried over anhydrous MgSO$_4$ and concentrated in vacuo. Purification by preparative thin layer chromatography afforded the title compound as a pale white solid (14.6 mg, 30% yield). $^1$H NMR (300 MHz, CDCl$_3$) δ 9.61, 8.78, 7.73, 7.58, 7.25, 6.78, 4.59, 3.95, 3.32, 3.13, 2.94. MS (ES+) m/z 484.0 (M+1).

EXAMPLE 3.1

The following compounds were synthesized by the similar procedure as described in Example 3:

1-(3-Methylbutyl)-3-{5-[4-(2-trifluoromethylbenzoyl)piperazin-1-yl]pyridin-2-yl}urea; $^1$H NMR (300 MHz, CDCl$_3$) δ 7.76-7.75 (m, 2H), 7.73-7.5.9 (m, 2H), 7.36-7.7.24 (m, 4H), 4.00-3.94 (m, 2H), 3.36-3.32 (m, 4H), 3.16 (t, 2H), 2.96 (t, 2H), 1.70-1.66 (m, 1H), 1.53-1.48 (m, 2H), 0.91 (d, 6H); MS (ES+) m/z 464.1 (M+1);

1-Butyl-3-{5-[4-(2-trifluoromethylbenzoyl)piperazin-1-yl]pyridin-2-yl}urea; $^1$H NMR (300 MHz, CDCl$_3$) δ 7.92-7.22 (m, 9H), 4.13-3.88 (m, 2H), 3.40-2.65 (m, 8H), 1.61-1.25 (m, 4H), 0.91 (t, 3H); MS (ES+) m/z 450.4 (M+1);

1-Phenethyl-3-{5-[4-(2-trifluoromethylbenzoyl)piperazin-1-yl]pyridin-2-yl}urea; $^1$H NMR (300 MHz, CDCl$_3$) δ 9.22 (s, 1H), 8.59 (s, 1H), 7.72 (d, 1H), 7.64-7.53 (m, 3H), 7.36-7.20 (m, 7H), 6.78 (d, 1H), 4.00-3.92 (m, 2H), 3.65-3.59 (m, 2H), 3.34 (t, 2H), 3.13 (t, 2H), 2.97-2.87 (m, 2H); MS (ES+) m/z 497.9 (M+1);

1-Pentyl-3-{5-[4-(2-trifluoromethylbenzoyl)piperazin-1-yl]pyridin-2-yl}urea; $^1$H NMR (CDCl$_3$) δ 7.78-7.77, 7.71-7.6, 7.57-7.54, 7.38-7.31, 6.91-6.88, 4.78, 3.86-3.65, 3.27-3.09, 2.95-2.94, 1.49-1.45, 1.28-1.24, 0.85-0.8; MS (ES+) m/z 464.2 (M+1);

1-[3-(4-Fluorophenyl)propyl]-3-{5-[4-(2-trifluoromethylbenzoyl)piperazin-1-yl]pyridin-2-yl}-urea; and 1-[3-(4-Fluorophenyl)propyl]-3-{5-[(2-trifluoromethylbenzoyl)piperazin-1-yl]pyridin-2-yl}-urea.

EXAMPLE 4

Synthesis of HEXANE-1-SULFONIC ACID {5-[4-(2-TRIFLUOROMETHYLBENZOYL)PIPERAZIN-1-YL]PYRIDIN-2-YL}AMIDE To a solution of [4-(6-aminopyridin-3-yl)piperazin-1-yl]-(2-trifluoromethylphenyl)-methanone (0.035 g, 0.10 mmol) in pyridine (3 mL) was added hexanesulfonyl chloride (0.022 mL, 0.12 mmol). After heating at 60° C. for 20 h, the mixture was diluted with ethyl acetate (100 mL), washed with brine, dried over anhydrous MgSO$_4$ and concentrated in vacuo. Purification by preparative thin layer chromatography afforded the title compound as a white solid (3.8 mg, 8% yield). $^1$H NMR (300 MHz, CDCl$_3$) δ 7.66, 7.29, 4.08, 3.91, 3.38, 3.27, 3.08, 1.84, 1.35, 1.27, 0.87. MS (ES+) m/z 499.4 (M+1).

EXAMPLE 4.1

The following compounds were synthesized by the similar procedure as described in Example 4:

Pentane-1-sulfonic acid {5-[4-(2-trifluoromethylbenzoyl)piperazin-1-yl]pyridin-2-yl}amide; $^1$H NMR (300 MHz, CDCl$_3$) δ 7.98 (s, 1H), 7.70 (d, 1H), 7.58-7.56 (m, 2H), 7.53-7.24 (m, 6H), 3.99-3.36 (m, 2H), 3.22-3.02 (m, 8H), 1.79-1.77 (m, 2H), 1.36-1.29 (m, 6H), 0.87 (t, 3H); MS (ES+) m/z 485.4 (M+1); and 3-Phenylpropane-1-sulfonic acid {5-[4-(2-trifluoromethylbenzoyl)piperazin-1-yl]pyridin-2-yl}amide.

EXAMPLE 5

Measuring Stearoyl-CoA Desaturase Inhibition Activity of a Test Compound Using Mouse Liver Microsomes The identification of compounds of the invention as SCD inhibitors was readily accomplished using the SCD enzymes and microsomal assay procedure described in Brownlie et al, PCT published patent application, WO 01/62954.

Preparation of Mouse Liver Microsomes:

Male ICR mice, on a high-carbohydrate, low fat diet, under light halothane (15% in mineral oil) anesthesia are sacrificed by exsanguination during periods of high enzyme activity. Livers are immediately rinsed with cold 0.9% NaCl solution, weighed and minced with scissors. All procedures are performed at 4° C. unless specified otherwise. Livers are homogenized in a solution (1:3 w/v) containing 0.25 M sucrose, 62 mM potassium phosphate buffer (pH 7.0), 0.15 M KCl, 1.5 mM N-acetyleysteine, 5 mM MgCl$_2$, and 0.1 mM EDTA using 4 strokes of a Potter-Elvehjem tissue homogenizer. The homogenate is centrifuged at 10,400×g for 20 min to eliminate mitochondria and cellular debris. The supernatant is filtered through a 3-layer cheesecloth and centrifuged at 105,000×g for 60 min. The microsomal pellet is gently resuspended in the same homogenization solution with a small glass/teflon homogenizer and stored at −70° C. The absence of mitochondrial contamination is enzymatically assessed. The protein concentration is measured using bovine serum albumin as the standard.

Incubation of Mouse Liver Microsomes with Test Compounds:

Reactions are started by adding 2 mg of microsomal protein to pre-incubated tubes containing 0.20 μCi of the substrate fatty acid (1-$^{14}$C palmitic acid) at a final concentration of 33.3 μM in 1.5 ml of homogenization solution, containing 42 mM NaF, 0.33 mM niacinamide, 1.6 mM ATP, 1.0 mM NADH, 0.1 mM coenzyme A and a 10 μM concentration of test compound. The tubes are vortexed vigorously and after 15 min incubation in a shaking water bath (37° C.), the reactions are stopped and fatty acids are analyzed.

Fatty acids are analyzed as follows: The reaction mixture is saponified with 10% KOH to obtain free fatty acids which are further methylated using $BF_3$ in methanol. The fatty acid methyl esters are analyzed by high performance liquid chromatography (HPLC) using a Hewlett Packard 1090, Series II chromatograph equipped with a diode array detector set at 205 nm, a radioisotope detector (Model 171, Beckman, Calif.) with a solid scintillation cartridge (97% efficiency for $^{14}$C-detection) and a reverse-phase ODS (C-18) Beckman column (250 mm×4.6 mm i.d.; 5 μm particle size) attached to a pre-column with a μBondapak C-18 (Beckman) insert. Fatty acid methyl esters are separated isocratically with acetonitrile/water (95:5 v:v) at a flow rate of 1 mL/min and are identified by comparison with authentic standards. Alternatively, fatty acid methyl esters may be analyzed by capillary column gas-chromatography (GC) or Thin Layer Chromatography (TLC).

Those skilled in the art are aware of a variety of modifications to this assay that can be useful for measuring inhibition of stearoyl-CoA desaturase activity in microsomes by test compounds.

Representative compounds of the invention showed activity as inhibitors of SCD when tested in this assay. The activity was defined in terms of % SCD enzyme activity remaining at the desired concentration of the test compound.

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method of inhibiting human stearoyl-CoA desaturase in vitro (hSCD) activity comprising contacting a source of hSCD with a compound of formula (I):

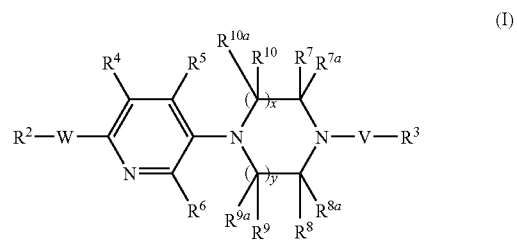

wherein:
x and y are each independently 1;
W is —C(O)N($R^1$)— or —N($R^1$)C(O)—;
V is —C(O)—;
each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;
$R^3$ is phenyl or naphthyl;
$R^4$, $R^5$ and $R^6$ are each independently selected from hydrogen, fluoro, chloro, methyl, methoxy, trifluoromethyl, cyano, nitro or —N($R^{13}$)$_2$;
$R^7$, $R^{7a}$, $R^8$, $R^{8a}$, $R^9$, $R^{9a}$, $R^{10}$ and $R^{10a}$ are each independently selected from hydrogen or $C_1$-$C_3$alkyl;
and
each $R^{13}$ is independently selected from hydrogen or $C_1$-$C_6$alkyl;
a stereoisomer, enantiomer or tautomer thereof, or a pharmaceutically acceptable salt thereof.

2. A method of alleviating a disease or condition mediated by stearoyl-CoA desaturase (SCD) in a mammal, wherein the method comprises administering to the mammal in need thereof a therapeutically effective amount of a compound of formula (I):

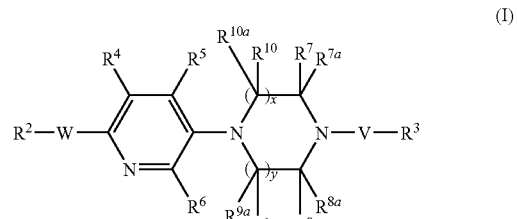

wherein:
x and y are each independently 1;
W is —C(O)N($R^1$)— or —N($R^1$)C(O)—;
V is —C(O)—;
each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

$R^3$ is phenyl or naphthyl;

$R^4$, $R^5$ and $R^6$ are each independently selected from hydrogen, fluoro, chloro, methyl, methoxy, trifluoromethyl, cyano, nitro or —N($R^{13}$)$_2$;

$R^7$, $R^{7a}$, $R^8$, $R^{8a}$, $R^9$, $R^{9a}$, $R^{10}$ and $R^{10a}$ are each independently selected from hydrogen or $C_1$-$C_3$alkyl; and each $R^{13}$ is independently selected from hydrogen or $C_1$-$C_6$alkyl;

a stereoisomer, enantiomer or tautomer thereof, or a pharmaceutically acceptable salt thereof, and wherein the disease or condition is selected from the group consisting of Type II diabetes, impaired glucose tolerance, insulin resistance, obesity, fatty liver, non-alcoholic steatohepatitis, dyslipidemia, acne, and any combination of these.

3. The method of claim 2 wherein the mammal is a human.

4. The method of claim 3, wherein the disease or condition is Type II diabetes.

5. The method of claim 3, wherein the disease or condition is obesity.

6. The method of claim 3, wherein the disease or condition is insulin resistance.

7. The method of claim 3, wherein the disease or condition is fatty liver.

8. The method of claim 3, wherein the disease or condition is non-alcoholic steatohepatitis.

9. A compound of formula (IIa):

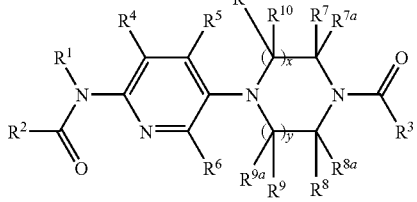

(IIa)

wherein:

x and y are each independently 1;

$R^1$ is selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_7$-$C_{12}$alkyl, $C_3$-$C_{12}$alkenyl, $C_7$-$C_{12}$hydroxyalkyl, $C_1$-$C_{12}$alkoxy, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_1$-$C_{12}$heteroaryl, $C_3$-$C_{12}$heterocyclylalkyl and $C_3$-$C_{12}$heteroarylalkyl, provided that $R^2$ is not pyrazinyl, pyridinonyl, pyrrolidinonyl or imidazolyl;

$R^3$ is phenyl or naphthyl;

$R^4$, $R^5$ and $R^6$ are each independently selected from hydrogen, fluoro, chloro, methyl, methoxy, trifluoromethyl, cyano, nitro or —N($R^{13}$)$_2$;

$R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl; and each $R^{13}$ is independently selected from hydrogen or $C_1$-$C_6$alkyl;

a stereoisomer, enantiomer or tautomer thereof, or a pharmaceutically acceptable salt thereof 10. The compound of claim 9 wherein:

x and y are each 1;

$R^1$ is hydrogen or $C_1$-$C_6$alkyl;

$R^2$ is selected from the group consisting of $C_7$-$C_{12}$alkyl, $C_3$-$C_{12}$alkenyl, $C_7$-$C_{12}$hydroxyalkyl, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_3$-$C_{12}$heterocyclylalkyl, and $C_3$-$C_{12}$heteroarylalkyl;

$R^3$ is phenyl or naphthyl;

$R^4$, $R^5$ and $R^6$ are each hydrogen; and $R^7$, $R^{7a}$, $R^8$, $R^{8a}$, $R^9$, $R^{9a}$, $R^{10}$, and $R^{10a}$ are each hydrogen.

11. A method of alleviating a disease or condition mediated by stearoyl-CoA desaturase (SCD) in a mammal, wherein the method comprises administering to a mammal in need thereof a therapeutically effective amount of a compound of claim 9, and wherein the disease or condition is selected from the group consisting of Type II diabetes, impaired glucose tolerance, insulin resistance, obesity, fatty liver, non-alcoholic steatohepatitis, dyslipidemia, acne, and any combination of these.

12. A pharmaceutical composition comprising a pharmaceutically acceptable excipient and a therapeutically effective amount of a compound of claim 9.

13. A compound of formula (IIb):

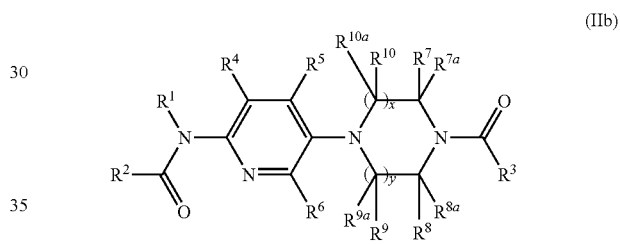

(IIb)

wherein:

x and y are each independently 1;

$R^1$ is selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl;

or $R^2$ is phenyl optionally substituted with one or more substituents selected from halo and $C_1$-$C_6$trihaloalkyl;

$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl, provided that $R^3$ is not phenyl substituted with optionally substituted thienyl;

$R^4$, $R^5$ and $R^6$ are each independently selected from hydrogen, fluoro, chloro, methyl, methoxy, trifluoromethyl, cyano, nitro or —N($R^{13}$)$_2$;

$R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl;

each $R^{12}$ is independently selected from hydrogen, $C_1$-$C_6$alkyl, $C_3$-$C_6$cycloalkyl, aryl or aralkyl; and each $R^{13}$ is independently selected from hydrogen or $C_1$-$C_6$alkyl;
a stereoisomer, enantiomer or tautomer thereof, or a pharmaceutically acceptable salt thereof.

14. The compound of claim 13 wherein:
x and y are each 1;
$R^1$ is hydrogen or $C_1$-$C_6$alkyl;
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_1$-$C_6$alkoxy, $C_3$-$C_{12}$alkoxyalkyl, $C_3$-$C_{12}$cycloalkyl, $C_4$-$C_{12}$cycloalkylalkyl, $C_7$-$C_{19}$aralkyl, $C_3$-$C_{12}$ heterocyclyl, $C_3$-$C_{12}$heterocyclylalkyl, $C_1$-$C_{12}$heteroaryl and $C_3$-$C_{12}$heteroarylalkyl;
or $R^2$ is phenyl optionally substituted with one or more substituents selected from halo or $C_1$-$C_6$trihaloalkyl;
$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$ and —S(O)$_2$N($R^{12}$)$_2$;
$R^4$, $R^5$ and $R^6$ are each hydrogen;
$R^7$, $R^{7a}$, $R^8$, $R^{8a}$, $R^9$, $R^{9a}$, $R^{10}$, and $R^{10a}$ are each hydrogen; and
each $R^{12}$ is independently selected from hydrogen, $C_1$-$C_6$alkyl, $C_3$-$C_6$cycloalkyl, aryl or aralkyl.

15. The compound of claim 14 wherein:
$R^2$ is $C_7$-$C_{12}$aralkyl optionally substituted by one or more substituents selected from the group consisting of halo, $C_1$-$C_3$alkyl and $C_1$-$C_6$trihaloalkyl; and
$R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

16. The compound of claim 15 selected from the group consisting of the following:
3-(4-Fluoro-phenyl)-N-{5-[4-(2-trifluoromethyl-benzoyl)-piperazin-1-yl]-pyridin-2-yl}-propionamide;
4-Phenyl-N-{5-[4-(2-trifluoromethyl-benzoyl)-piperazin-1-yl]-pyridin-2-yl}-butyramide;
4-(4-Fluoro-phenyl)-N-{5-[4-(2-trifluoromethyl-benzoyl)-piperazin-1-yl]-pyridin-2-yl}-butyramide; and
3-Phenyl-N-{5-[4-(2-trifluoromethyl-benzoyl)-piperazin-1-yl]-pyridin-2-yl}-propionamide.

17. The compound of claim 14 wherein:
$R^2$ is $C_1$-$C_{12}$alkyl or $C_2$-$C_{12}$alkenyl; and
$R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

18. The compound of claim 17 selected from the group consisting of the following:
Hexanoic acid {5-[4-(2-trifluoromethyl-benzoyl)-piperazin-1-yl]-pyridin-2-yl}-amide;
Heptanoic acid {5-[4-(2-trifluoromethyl-benzoyl)-piperazin-1-yl]-pyridin-2-yl}-amide; and 5-Methylpentanoic acid {5-[4-(2-trifluoromethyl-benzoyl)-piperazin-1-yl]-pyridin-2-yl}-amide.

19. The compound of claim 14 wherein:
$R^2$ is $C_3$-$C_{12}$heteroarylalkyl optionally substituted by one or more substituents selected from the group consisting of halo, $C_1$-$C_3$alkyl and $C_1$-$C_6$trihaloalkyl; and
$R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

20. The compound of claim 19, namely, 3-Pyridin-3-yl-N-{5-[4-(2-trifluoromethyl-benzoyl)-piperazin-1-yl]-pyridin-2-yl}-propionamide.

21. The compound of claim 14 wherein:
$R^2$ is phenyl optionally substituted with one or more substituents selected from halo and $C_1$-$C_6$trihaloalkyl; and
$R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy.

22. The compound of claim 21, namely, 4-Fluoro-N-{5-[4-(2-trifluoromethylbenzoyl)piperazin-1-yl]pyridin-2-yl}benzamide.

23. A method of alleviating a disease or condition mediated by stearoyl-CoA desaturase (SCD) in a mammal, wherein the method comprises administering to a mammal in need thereof a therapeutically effective amount of a compound of claim 13, wherein the disease or condition is selected from the group consisting of Type II diabetes, impaired glucose tolerance, insulin resistance, obesity, fatty liver, non-alcoholic steatohepatitis, dyslipidemia, acne, and any combination of these.

24. A pharmaceutical composition comprising a pharmaceutically acceptable excipient and a therapeutically effective amount of a compound of claim 13.

25. A compound of formula (VIa):

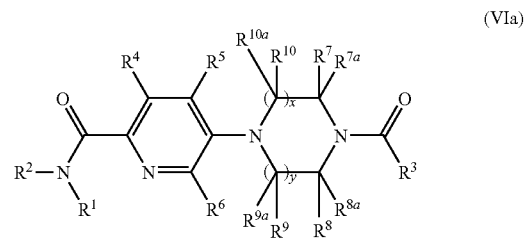

(VIa)

wherein:
x and y are each independently 1;
$R^1$ is selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;
$R^2$ is selected from the group consisting of $C_7$-$C_{12}$alkyl, $C_3$-$C_{12}$alkenyl, $C_7$-$C_{12}$hydroxyalkyl, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_3$-$C_{12}$heterocyclylalkyl, and $C_3$-$C_{12}$heteroarylalkyl;
$R^3$ is phenyl or naphthyl;
$R^4$, $R^5$ and $R^6$ are each independently selected from hydrogen, fluoro, chloro, methyl, methoxy, trifluoromethyl, cyano, nitro or —N($R^{13}$)$_2$;
$R^7$, $R^{7a}$, $R^8$, $R^{8a}$, $R^9$, $R^{9a}$, $R^{10}$, and $R^{10a}$ are each independently selected from hydrogen or $C_1$-$C_3$alkyl; and
each $R^{13}$ is independently selected from hydrogen or $C_1$-$C_6$alkyl;
including a stereoisomer, enantiomer or tautomer thereof, or a pharmaceutically acceptable salt thereof.

26. The compound of claim 25 wherein:
x and y are each 1;
$R^1$ is hydrogen or $C_1$-$C_6$alkyl;
$R^2$ is selected from the group consisting of $C_7$-$C_{12}$alkyl, $C_3$-$C_{12}$alkenyl, $C_7$-$C_{12}$hydroxyalkyl, $C_2$-$C_{12}$alkoxyalkyl, $C_3$-$C_{12}$hydroxyalkenyl, $C_3$-$C_{12}$cycloalkyl, $C_4$-$C_{12}$cycloalkylalkyl, $C_{13}$-$C_{19}$aralkyl, $C_3$-$C_{12}$heterocyclylalkyl, and $C_3$-$C_{12}$heteroarylalkyl;

R³ is phenyl or naphthyl;
R⁴, R⁵ and R⁶ are each hydrogen; and
R⁷, R⁷ᵃ, R⁸, R⁸ᵃ, R⁹, R⁹ᵃ, R¹⁰, and R¹⁰ᵃ are each hydrogen.

27. A method of alleviating a disease or condition mediated by stearoyl-CoA desaturase (SCD) in a mammal, wherein the method comprises administering to a mammal in need thereof a therapeutically effective amount of a compound of claim 25, and wherein the disease or condition is selected from the group consisting of Type II diabetes, impaired glucose tolerance, insulin resistance, obesity, fatty liver, non-alcoholic steatohepatitis, dyslipidemia, acne, and any combination of these.

28. A pharmaceutical composition comprising a pharmaceutically acceptable excipient and a therapeutically effective amount of a compound of claim 25.

29. A compound of formula (VIb):

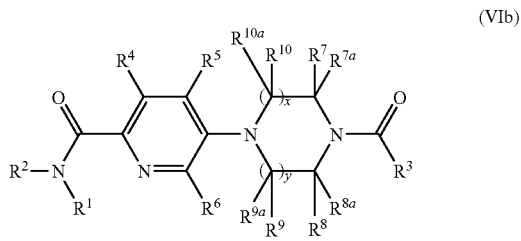

(VIb)

wherein:
x and y are each independently 1;
each R¹ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;
R² is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;
R³ is naphthyl or phenyl, each optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N(R¹²)₂, —OC(O)R¹², —C(O)OR¹², —S(O)₂N(R¹²)2, cycloalkyl, heterocyclyl, heteroaryl and heteroarylcycloalkyl, provided that R³ is not phenyl substituted with optionally substituted thienyl, and provided that when R³ is naphthyl, R² can not be $C_1$-$C_6$alkyl, $C_2$-$C_6$hydroxyalkyl or phenyl substituted by amino;
R⁴, R⁵ and R⁶ are each independently selected from hydrogen, fluoro, chloro, methyl, methoxy, trifluoromethyl, cyano, nitro or —N(R¹³)₂;
R⁷, R⁷ᵃ, R⁸, R⁸ᵃ, R⁹, R⁹ᵃ, R¹⁰, and R¹⁰ᵃ are each independently selected from hydrogen or $C_1$-$C_3$alkyl;
each R¹² is independently selected from hydrogen, $C_1$-$C_6$alkyl, $C_3$-$C_6$cycloalkyl, aryl or aralkyl; and
each R¹³ is independently selected from hydrogen or $C_1$-$C_6$alkyl;
a stereoisomer, enantiomer or tautomer thereof, or a pharmaceutically acceptable salt thereof.

30. The compound of claim 29 wherein:
x and y are each 1;
R¹ is hydrogen or $C_1$-$C_6$alkyl;
R² is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_3$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;
R³ is naphthyl or phenyl, each optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N(R¹²)₂, —OC(O)R¹², —C(O)OR¹² or —S(O)₂N(R¹²)₂;
R⁴, R⁵ and R⁶ are each hydrogen;
R⁷, R⁷ᵃ, R⁸, R⁸ᵃ, R⁹, R⁹ᵃ, R¹⁰, and R¹⁰ᵃ are each hydrogen; and
each R¹² is independently selected from hydrogen, $C_1$-$C_6$alkyl, $C_3$-$C_6$cycloalkyl, aryl or aralkyl.

31. The compound of claim 30 wherein:
R² is $C_7$-$C_{12}$aralkyl optionally substituted by one or more substituents selected from the group consisting of halo, $C_1$-$C_3$alkyl and $C_1$-$C_6$trihaloalkyl; and
R³ is phenyl optionally substituted by one or more substituents selected from the group consisting of halo, $C_1$-$C_6$alkyl, $C_1$-$C_6$trihaloalkyl and $C_1$-$C_6$trihaloalkoxy.

32. The compound of claim 31 selected from the group consisting of the following:
  5-[4-(2-Trifluoromethyl-benzoyl)-piperazin-1-yl]-pyridine-2-carboxylic acid (3-phenyl-propyl)-amide;
  5-[4-(2-Trifluoromethyl-benzoyl)-piperazin-1-yl]-pyridine-2-carboxylic acid phenethyl-amide;
  5-[4-(2-Trifluoromethylbenzoyl)piperazin-1-yl]pyridine-2-carboxylic acid [2-(4-fluoro-phenyl)ethyl]amide;
  5-[4-(2-Trifluoromethyl-benzoyl)-piperazin-1-yl]-pyridine-2-carboxylic acid [3-(4-fluoro-phenyl)-propyl]-amide;
  5-[4-(2-Trifluoromethyl-benzoyl)-piperazin-1-yl]-pyridine-2-carboxylic acid 4-trifluoromethyl-benzylamide;
  5-[4-(2-Trifluoromethyl-benzoyl)-piperazin-1-yl]-pyridine-2-carboxylic acid [3-(4-trifluoromethyl-phenyl)-propyl]-amide; and
  5-[4-(2-Trifluoromethyl-benzoyl)-piperazin-1-yl]-pyridine-2-carboxylic acid [2-(4-trifluoromethyl-phenyl)-ethyl]-amide.

33. The compound of claim 30 wherein:
R² is $C_1$-$C_{12}$alkyl or $C_2$-$C_{12}$alkenyl; and
R³ is phenyl optionally substituted by one or more substituents selected from the group consisting of halo, $C_1$-$C_6$alkyl, $C_1$-$C_6$trihaloalkyl and $C_1$-$C_6$trihaloalkoxy.

34. The compound of claim 33 selected from the group consisting of the following:
  5-[4-(2-Trifluoromethyl-benzoyl)-piperazin-1-yl]-pyridine-2-carboxylic acid (3-methyl-butyl)-amide;
  5-[4-(2-Trifluoromethyl-benzoyl)-piperazin-1-yl]-pyridine-2-carboxylic acid hexylamide;
  5-[4-(2-Trifluoromethyl-benzoyl)-piperazin-1-yl]-pyridine-2-carboxylic acid pentylamide;
  5-[4-(4-Fluoro-2-trifluoromethyl-benzoyl)-piperazin-1-yl]-pyridine-2-carboxylic acid (3-methyl-butyl)-amide; and
  5-[4-(5-Fluoro-2-trifluoromethyl-benzoyl)-piperazin-1-yl]-pyridine-2-carboxylic acid (3-methyl-butyl)-amide.

35. The compound of claim 30 wherein:
R² is $C_3$-$C_{12}$cycloalkyl or $C_4$-$C_{12}$cycloalkylalkyl; and
R³ is phenyl optionally substituted by one or more substituents selected from the group consisting of halo, $C_1$-$C_6$alkyl, $C_1$-$C_6$trihaloalkyl and $C_1$-$C_6$trihaloalkoxy.

36. The compound of claim 35 selected from the group consisting of the following:
- 5-[4-(2-Trifluoromethylbenzoyl)piperazin-1-yl]pyridine-2-carboxylic acid (3-cyclohexyl-propyl)amide;
- 5-[4-(6-Trifluoromethyl-cyclohexa-1,3-dienecarbonyl)-piperazin-1-yl]-pyridine-2-carboxylic acid (2-cyclohexyl-ethyl)-amide; and
- 5-[4-(2-Trifluoromethyl-benzoyl)-piperazin-1-yl]-pyridine-2-carboxylic acid cyclohexylmethyl-amide.

37. The compound of claim 30 wherein:
$R^2$ is $C_3$-$C_{12}$heterocyclylalkyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —$N(R^{12})_2$, —$OC(O)R^{12}$, —$C(O)OR^{12}$ and —$S(O)_2N(R^{12})_2$;
$R^3$ is phenyl optionally substituted by one or more substituents selected from the group consisting of halo, $C_1$-$C_6$alkyl, $C_1$-$C_6$trihaloalkyl and $C_1$-$C_6$trihaloalkoxy; and
each $R^{12}$ is independently selected from hydrogen, $C_1$-$C_6$alkyl, $C_3$-$C_6$cycloalkyl, aryl or aralkyl.

38. The compound of claim 37 wherein $R^2$ is 2-piperazinylethyl optionally substituted by —$C(O)OR^{12}$.

39. The compound of claim 38, namely, 4-[2-({5-[4-(2-Trifluoromethyl-benzoyl)-piperazin-1-yl]-pyridine-2-carbonyl}-amino)-ethyl]-piperazine-1-carboxylic acid tert-butyl ester.

40. The compound of claim 30 wherein:
$R^2$ is $C_7$-$C_{12}$aralkyl optionally substituted by one or more substituents selected from the group consisting of halo, $C_1$-$C_3$alkyl and $C_1$-$C_6$trihaloalkyl; and
$R^3$ is naphthyl optionally substituted by one or more substituents selected from the group consisting of halo, $C_1$-$C_6$alkyl, $C_1$-$C_6$trihaloalkyl and $C_1$-$C_6$trihaloalkoxy.

41. The compound of claim 40 selected from the group consisting of the following:
- 5-[4-(Naphthalene-1-carbonyl)-piperazin-1-yl]-pyridine-2-carboxylic acid (3-phenyl-propyl)-amide; and
- 5-[4-(Naphthalene-1-carbonyl)piperazin-1-yl]pyridine-2-carboxylic acid phenethylamide.

42. A method of alleviating a disease or condition mediated by stearoyl-CoA desaturase (SCD) in a mammal, wherein the method comprises administering to a mammal in need thereof a therapeutically effective amount of a compound of claim 29, wherein the disease or condition is selected from the group consisting of Type II diabetes, impaired glucose tolerance, insulin resistance, obesity, fatty liver, non-alcoholic steatohepatitis, dyslipidemia, acne, and any combination of these.

43. A pharmaceutical composition comprising a pharmaceutically acceptable excipient and a therapeutically effective amount of a compound of claim 29.

* * * * *

UNITED STATES PATENT AND TRADEMARK OFFICE
CERTIFICATE OF CORRECTION

PATENT NO. : 7,763,618 B2
APPLICATION NO. : 10/566857
DATED : July 27, 2010
INVENTOR(S) : Melwyn Abreo et al.

It is certified that error appears in the above-identified patent and that said Letters Patent is hereby corrected as shown below:

In Claim 29, Column 51, Line 47, "$-S(O)_2N(R^{12})2$" should read: "$-S(O)_2N(R^{12})_2$".

Signed and Sealed this

Thirtieth Day of November, 2010

David J. Kappos
*Director of the United States Patent and Trademark Office*